United States Patent [19]

Strupczewski et al.

[11] Patent Number: 4,954,503
[45] Date of Patent: Sep. 4, 1990

[54] 3-(1-SUBSTITUTED-4-PIPERAZINYL)-1H-INDAZOLES

[75] Inventors: Joseph T. Strupczewski, Flemington, N.J.; Kenneth J. Bordeau, Upper Black Eddy, Pa.

[73] Assignee: Hoechst-Roussel Pharmaceuticals, Inc., Somerville, N.J.

[21] Appl. No.: 405,161

[22] Filed: Sep. 11, 1989

[51] Int. Cl.$^5$ ............... A61K 31/495; C07D 401/14; C07D 403/04; C07D 403/14

[52] U.S. Cl. .................... 514/254; 544/230; 544/232; 544/366; 544/368

[58] Field of Search .............. 544/230, 232, 366, 368; 514/254

[56] References Cited

U.S. PATENT DOCUMENTS

| | | | |
|---|---|---|---|
| 4,260,610 | 4/1981 | Regnier et al. | 544/368 |
| 4,452,799 | 6/1984 | Temple, Jr. et al. | 544/368 |
| 4,524,206 | 6/1985 | New et al. | 544/368 |
| 4,536,578 | 8/1985 | Davis et al. | 544/368 |
| 4,590,196 | 5/1986 | Smith et al. | 544/368 |
| 4,737,500 | 4/1988 | Soy | 544/368 |

OTHER PUBLICATIONS

Strupczewski et al., Chem. Abst. 110-212857z (1989).
Wrzeciono et al., Chem. Abst. 112-55915p (1990).
Wrzeciono et al., CA 106-176242b, Chemical Abstracts, 11th Col. Index, (vol. 96-105, 1982-1986, p. 34189cs).
Lowe et al., CA 110-39024a (1989).
Wrzeciono et al., CA 111-77999a (1989).

*Primary Examiner*—Cecilia Shen
*Attorney, Agent, or Firm*—Elliott Korsen; Jerome Rosenstock

[57] ABSTRACT

This invention relates to 3-(1-substituted-4-piperazinyl)-1H-indazoles having the following formula

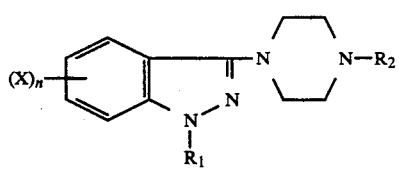

wherein $R_1$ is hydrogen, lower alkyl, arylloweralkyl, acyl, cycloalkylloweralkylene, and phenylsulfonyl; and $R_2$ is hydrogen, lower alkyl, hydroxyloweralkyl of the formula -(loweralkylene)-OH, arylloweralkyl, acyl, cycloalkylloweralkylene, 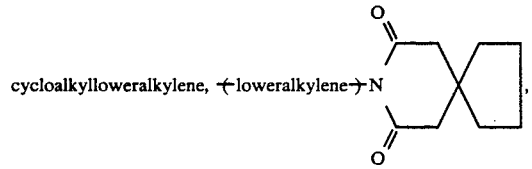

-continued

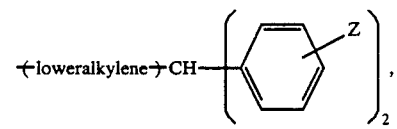

where Z is selected from hydrogen, halogen, loweralkoxy, $CF_3$, $NO_2$, and $NH_2$;

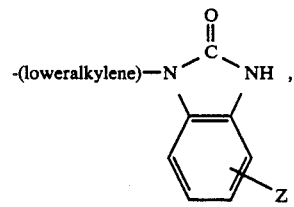

where Z is as defined above;

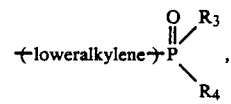

where Z is as defined above;

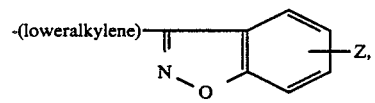

where $R_3$ and $R_4$ are each independently hydrogen and loweralkyl;

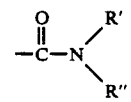

where Z is as defined above;

$$-\overset{O}{\underset{\|}{C}}-N\overset{R'}{\underset{R''}{\diagdown}}$$

where R' and R" are each independently hydrogen and loweralkyl; X is hydrogen, loweralkyl, hydroxyl, halogen, loweralkoxy, $CF_3$, $NO_2$ and amino; n is an integer of 1 to 4, with the further proviso that $R_2$ is not loweralkyl when $R_1$ is hydrogen or acyl and X is chloro; the pharmaceutically acceptable acid addition salts thereof and where appropriate the geometric isomers, the stereoisomers and racemic mixtures thereof. The compounds of this invention display utility as analgesic and antipsychotic agents.

187 Claims, No Drawings

3-(1-SUBSTITUTED-4-PIPERAZINYL)-1H-INDAZOLES

This invention relates to compounds of the formula

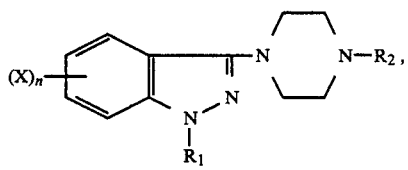
(I)

wherein $R_1$ is hydrogen, lower alkyl, arylloweralkyl, acyl, cycloalkylloweralkylene and phenylsulfonyl; and $R_2$ is hydrogen, lower alkyl, hydroxyloweralkyl of the formula −(loweralkylene)−OH, arylloweralkyl, acyl, cycloalkylloweralkylene, 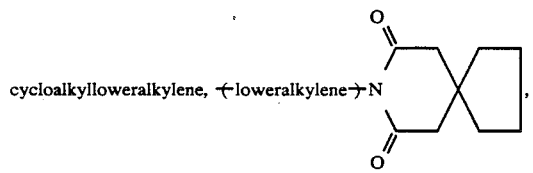

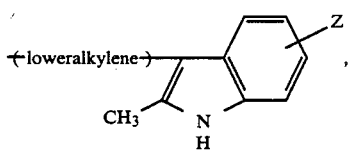

where Z is selected from hydrogen, halogen, loweralkoxy, $CF_3$, $NO_2$, and $NH_2$;

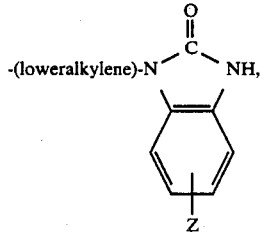

where Z is as defined above;

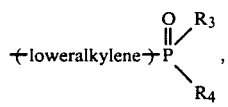

where Z is as defined above;

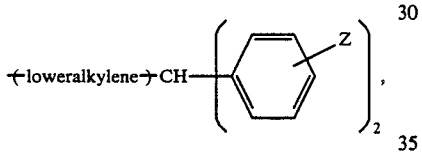

where $R_3$ and $R_4$ are independently hydrogen and loweralkyl;

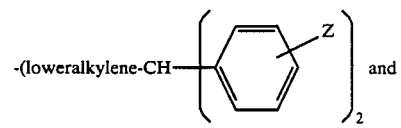

where Z is as defined above;

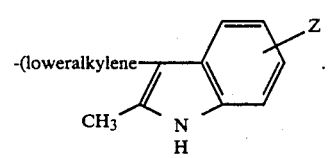

where R' and R" are independently hydrogen and loweralkyl; X is hydrogen, loweralkyl, hydroxyl, halogen, loweralkoxy, $CF_3$, $NO_2$ and amino; n is an integer of 1 to 4 with the further proviso that $R_2$ is not loweralkyl when $R_1$ is hydrogen or acyl and X is chloro.

Preferred embodiments are Compound I where $R_1$ is selected from H, alkyl, and benzoyl; and $R_2$ is selected from alkyl,

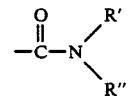 and

Most preferred is where $R_1$ is hydrogen and methyl and $R_2$ is methyl and 4,4-bis(4-fluorophenyl)butyl.

Throughout the specification and appended claims, a given chemical formula or name shall encompass all geometric and stereoisomers thereof where such isomers exist.

In the above definition, the term, "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc.; the term "arylloweralkyl" refers to a monovalent substituent which consists of an aryl group, e.g. phenyl, o-toluyl, m-methoxyphenyl, etc., of the formula,

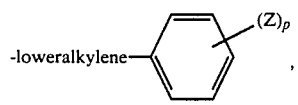

where Z is as defined below, linked through a loweralkylene group having its free valence bond from a carbon of the loweralkylene group, and having a formula of

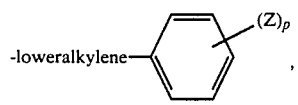

where Z is hydrogen, halogen, loweralkyl, loweralkoxy, CF₃, NO₂ and NH₂ and p is an integer of 1 to 4; the term "alkylene" refers to a bivalent radical of the lower branched or unbranched alkyl group it is derived from having the valence bonds from two terminal carbons thereof, e.g. ethylene (—CH₂CH₂—), propylene (—CH₂CH₂CH₂—),

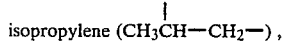

isopropylene (CH₃CH—CH₂—), etc; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc; the term "acyl" refers to a substituent having the formula

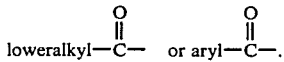

loweralkyl—C—  or  aryl—C—.

the term "cycloalkylloweralkylene" refers to a saturated hydrocarbon possessing at least one carbocyclic ring of three to seven carbon atoms, e.g. cyclopropyl, cyclobutyl, cyclopentyl, cyclohexyl, cycloheptyl, etc., linked through a lower alkylene group, and having a formula of

-loweralkylene—⟨(CH₂)ₘ⟩, where m is an integer of 1 to 5; and the term "halogen" refers to a member of the halogen family consisting of fluorine, chlorine, bromine and iodine.

The compounds of the present invention are prepared in the following manner. The substituents R₁, R₂, R₃, R₄, X and Z and the integers m, n and p are as defined above unless indicated otherwise.

A substituted aryl ester of formula II is selected,

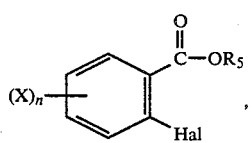

(II)

where R₅ is loweralkyl and Hal is a halogen selected from Cl, Br and I. Ester II is reacted with hydrazine, H₂NNH₂, under standard hydrazide forming conditions. Typically, the reaction is carried out in a nonreactive solvent, e.g. ethanol, methanol, toluene, etc. at a temperature of ambient to reflux of the solvent for 4 to 16 hours to form a hydrazide of the formula (III),

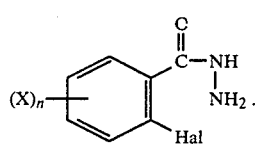

(III)

Compound III is reacted with a phenyl sulfonyl halide

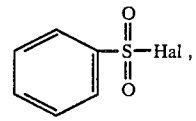

(IV)

where Hal is a halogen selected from Cl and Br, to form Compound (V),

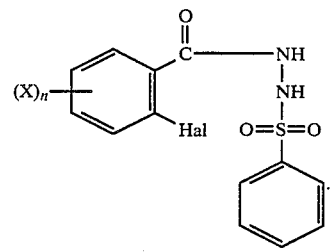

(V)

Typically this reaction is carried out in a basic solvent, e.g. pyridine, collidine, etc., at a temperature of 0° to 30° C. for 2 to 16 hours. Compound V in turn is reacted neat with thionyl chloride at a temperature of 50° to 79° C. (reflux temperature) for 2 to 16 hours to form Compound (VI)

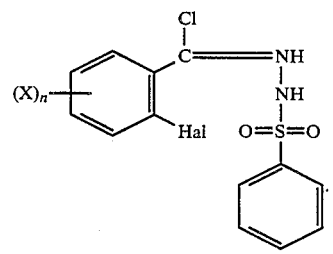

(VI)

Compound VI is reacted with Compound VII,

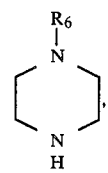

where R₆ is loweralkyl, under conventional nucleophilic reaction conditions, such as for example in an inert solvent such as tetrahydrofuran (THF), toluene, diethylether, etc., at a temperature of 5° to 50° C. for 1 to 16 hours to form a compound having the formula

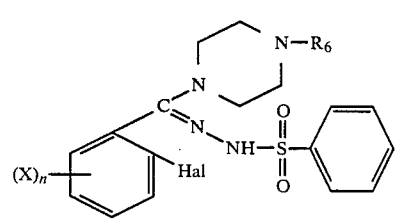

(VIII)

Compound VI can also be reacted neat, i.e., without a solvent, with excess of Compound VII to form Compound VIII. Compound VIII is then reacted with a condensation agent such as copper, copper-bronze, cuprous oxide, etc. in a solvent such as dimethylformamide, dimethylacetamide, tetramethylurea, etc., at a temperature of 120° to 177° C. for 1 to 16 hours to form a piperazine substituted phenylsulfonyl indazole of the formula

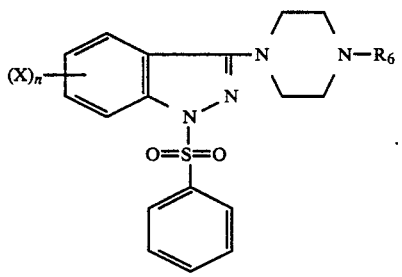
(IX)

A cyano-substituted piperazine phenylsulfonyl indazole is then formed by reacting Compound IX with a conventional cyanylation source, such as a halo-cyanide, e.g. BrCN, ClCN, etc., under conventional cyanylation conditions, typically in an inert solvent, e.g. dimethylsulfoxide (DMSO), CHCl$_3$, etc. at ambient temperature for 2 to 16 hours to form Compound X, of the formula

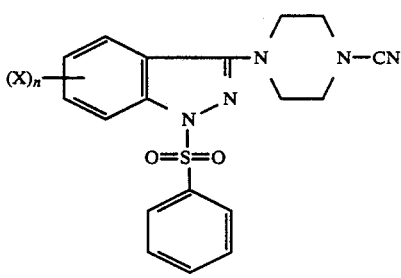
(X)

Compound X is then subjected to reduction by means of a metal hydride, e.g. LiAlH$_4$. Typically the reduction is carried out under standard reduction conditions in a solvent, such as tetrahydrofuran (THF), diethyl ether, etc., at a temperature of 35° to 67° C. for 6 to 16 hours to form a compound of the invention, (Compound I where R$_1$ and R$_2$ are both hydrogen),

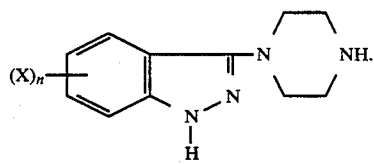
(XI)

Compound XI can be formed in an alternative manner by first reacting Compound IX with a strong base, such as a metal alcoholate, e.g. sodium methoxide, sodium ethoxide, sodium butoxide, etc., or with KOH in tetrahydrofuran to form Compound XII of the invention (Compound I, where R$_1$ is hydrogen and R$_2$ is lower alkyl),

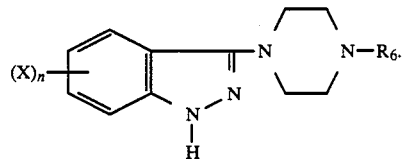
(XII)

When a metal alcoholate is used, this reaction is typically carried out in a polar solvent, such as for example CH$_3$OH, C$_2$H$_5$OH, etc., at a temperature of ambient to 50° C. for 1 to 16 hours. Alternatively, Compound XII can be formed by reducing compound (IX) with LiAlH$_4$, under conditions as previously described. Compound XII in turn is reacted with a cyanylation reagent, as previously described, to form a cyano-substituted piperazine indazole of the formula

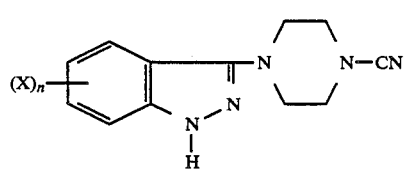
(XIII)

which in turn is reduced with a metal hydride, as previously described, to form Compound XI of the invention.

In an alternative embodiment, Compound XIII is reacted with an aqueous mineral acid, e.g. H$_2$SO$_4$, HCl, etc., at a temperature of 50° to 120° C., for 2 to 16 hours to form Compound XI of the invention.

Compound XI of the invention can be further reacted under conventional nucleophilic reaction conditions with a compound having the formula R$_7$Y, [(XIV)] where R$_7$ is loweralkyl, arylloweralkyl, cycloalkyl-loweralkylene,

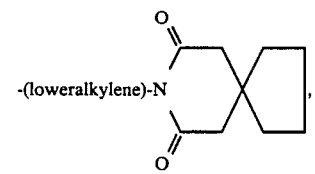

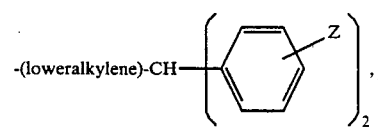

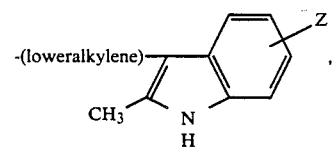

-continued

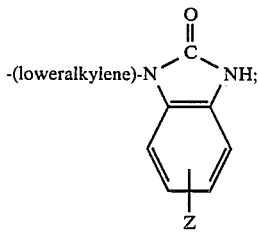

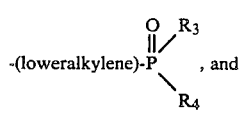

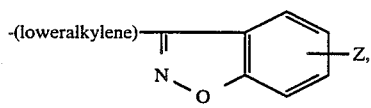

and Y is a halogen selected from Cl and Br, to form compound XV of the formula

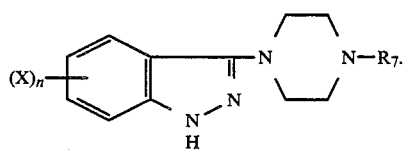

Compound XI is reacted with a compound of the formula $R_8$ Hal (XVI), where $R_8$ is HO-loweralkylene and Hal is a halogen selected from Cl and Br to form Compound XVII,

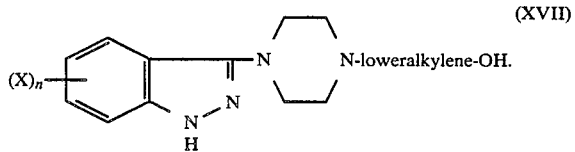

Typically the reaction is carried out in an inert solvent, e.g. dimethylformamide (DMF), $CH_3CN$, etc., at a temperature of 50° to 100° C. for 4 to 16 hours.

Compound XII is reacted with a compound of the formula

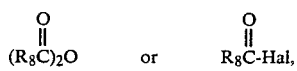

where Hal is a halogen selected from Cl and Br, and $R_8$ is selected from lower alkyl or aryl, under conventional acylation conditions, e.g. in an inert solvent such as $CHCl_3$, toluene, etc., in the presence of an inert base, e.g. $K_2CO_3$, etc., at a temperature of 0° C. to the reflux temperature of the solvent, to form a compound of the formula

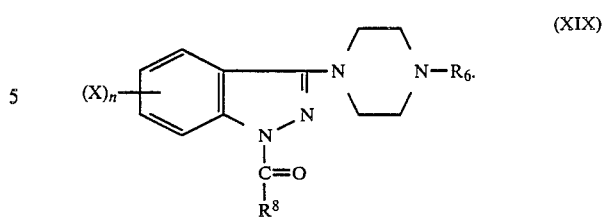

Compound XII is reacted with a compound of the formula $R_9$Hal, where $R_9$ is selected from loweralkyl, arylloweralkyl and cycloalkylloweralkyl, and Hal is a halogen selected from Cl and Br to form Compound XX

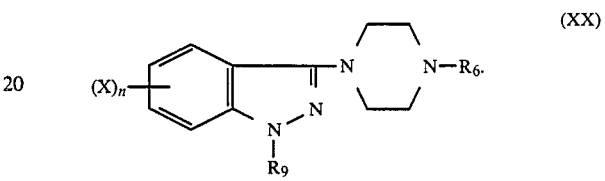

Typically the reaction is carried out in an aprotic solvent, e.g. DMF, dimethylacetamide, etc., in the presence of a base, such as NaH, KH, etc., at a temperature of 25° to 50° C. for 2 to 16 hours.

Compounds of the invention include 3-(4-cyclopropylmethyl-1-piperazinyl)-1H-indazole;
3-[4-(2-propenyl)-1-piperazinyl]-1H-indazole;
3-(4-acetyl-1-piperazinyl)-6-fluoro-1H-indazole;
3-(4-phenylmethyl-1-piperazinyl)-1H-indazole;
3-(4-butyl-1-piperazinyl)-6-fluoro-1H-indazole;
5-bromo-3-(1-piperazinyl)-1H-indazole;
3-[4-[2-(diethylamino)ethyl]-1-piperazinyl]-1H-indazole;
3-[4-[2-(dimethylamino)ethyl]-1-piperazinyl]-6-fluoro-1H-indazole;
3-(4-methyl-1-piperazinyl)-5-nitro-1H-indazole;
3-(4-methyl-1-piperazinyl)-5-trifluoromethyl-1H-indazole;
5-amino-(4-methyl-1-piperazinyl)-1H-indazole;
3-(4-benzoyl-1-piperazinyl)-1H-indazole;
3-(4-methyl-1-piperazinyl)-1-phenylmethyl-1H-indazole;
5-hydroxy-(4-methyl-1-piperazinyl)-1H-indazole;
N-methyl-4-(1H-indazol-3-yl)-1-piperazinecarboxamide;
5,6-dimethoxy-3-(4-methyl-1-piperazinyl)-1H-indazole;
5-fluoro-3-(4-methyl-1-piperazinyl)-1H-indazole;

Compounds of the present invention are useful as analgesic agents due to their ability to alleviate pain in mammals. The activity of the compounds is demonstrated in the 2-phenyl-1,4-benzoquinone-induced writhing test in mice, a standard assay for analgesia [Proc. Soc. Exptl. Biol. Med. 95,729 (1957)]. The analgesic activity of some of the compounds expressed in terms of $ED_{50}$ values for inhibition of writhing are given in TABLE I.

TABLE I

| Compound | Dose (subcutaneous) (mg/kg of body weight [ED50] |
|---|---|
| 3-(4-methyl-1-piperazinyl)-1H-indazole | 0.04 |
| 1-ethyl-3-(4-methyl-1-piperazinyl)-1H-indazole | 0.5 |

TABLE I-continued

| Compound | Dose (subcutaneous) (mg/kg of body weight [ED50] |
|---|---|
| 8-[4-[1-(1H-indazol-3-yl)-4-piperazinyl]butyl-8-azaspiro[4.5]decane-7,9-dione hemifumarate | 0.07 |
| 1-cyclopropylmethyl-3-(4-methyl-1-piperazinyl)-1H-indazole | 1.5 |
| 3-[4-[4,4-bis(4-fluorophenyl)butyl]-1-piperazinyl]-1H-indazole hydrochloride | 3.6 |
| 3-(1-piperazinyl)-1H-indazole | 0.9 |
| 1-benzoyl-6-fluoro-3-(4-methyl-1-piperazinyl)-1H-indazole | 4.3 |
| 3-[4-(2-hydroxyethyl)-1-piperazinyl]-1H-indazole dihydrochloride | 2.0 |
| 1-acetyl-3-(4-methyl-1-piperazinyl)-1H-indazole | 2.1 |
| 5-chloro-3-(4-methyl-1-piperazinyl)-1H-indazole | 6.8 |
| propoxyphene (standard) | 3.9 |

The analgesic relief of pain is achieved when the compounds of the invention are administered to a subject requiring such treatment at an effective oral, parenteral or intravenous dose of from 0.1 to 25 mg/kg of body weight per day. A preferred effective dose within the range is from about 1 to 10 mg/kg of body weight per day. A particularly preferred effective amount is about 2 mg/kg of body weight per day. It is to be understood, however, that for any particular subject, specific dosage regimens should be adjusted according to the individual need. It is further to be understood that the dosage set forth herein are examples only and that they do not to any extent, limit the scope of practice of the invention.

The compounds of the present invention are also useful as antipsychotic agents.

Antipsychotic activity is determined in the climbing mice assay by methods similar to those described by P. Protais, et al., Psychopharmacol, 50, 1 (1976) and B. Costall, Eur. J. Pharmacol., 50, 39 (1978).

The subject CK-1 male mice (23-27 grams) are group-housed under standard laboratory conditions. The mice are individually placed in wire mesh stick cages (4"×4"×10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior Mice With | Score |
|---|---|
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With full-developed apomorphine climbing, the animals are hanging onto the cage walls, rather motionless over longer periods of time. By contrast, climbs due to mere motor stimulation usually last only a few seconds.

The climbing scores are individually totaled (maximum score: 6 per mouse over 3 readings) and the total score of the control group (vehicle intraperitoneally-apomorphine subcutaneously) is set to 100%. $ED_{50}$ values with 95% confidence limits, calculated by a linear regression analysis of some of the compounds of this invention are presented in Table II.

TABLE II

| COMPOUND | Antipsychotic Activity (Climbing Mice Assay) $ED_{50}$ mg/kg ip |
|---|---|
| 8-[4-[1-(1H-indazol-3-yl)-4-piperazinyl]butyl-8-azaspiro[4,5]decane-7,9-dione hemifumarate | 0.6 |
| 3-[4-[4,4-bis(4-fluorophenyl)butyl]-1-piperazinyl]-1H-indazole hydrochloride | 0.87 |
| 8-[4-[1-(1-methyl-1H-indazol-3-yl)-4-piperazinyl]butyl-8-azaspiro[4.5]decane-7,9-dione fumarate | 7.3 |
| 6-fluoro-3-(4-methyl-1-piperazinyl)-1H-indazole | 4.7 |
| 3-[4-[3-(2-methylindole-3-yl)propyl]-1-piperazinyl]-1H-indazole hemifumarate | 0.4 |
| 6-fluoro-3-(1-piperazinyl)-1H-indazole hydrochloride | 6.4 |
| 6-fluoro-3-[4-[3-(1,3-dihydro-2-oxo-2H-benzimidazol-1-yl)propyl]-1-piperazinyl]-1H-indazole hemifumarate | 0.43 |
| haloperidol (standard) | 0.11 |
| sulpiride (standard) | 14.5 |

Antipsychotic response is achieved when the compounds of the invention are administered to a subject requiring such treatment at an effective oral, prenteral or intravenous dose of from 0.1 to 50 mg/kg of body weight per day. A preferred effective dose within this range is from about 0.1 to 5 mg/kg of body weight per day. A particularly preferred effective amount is about 1 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosage set forth herin are examples only and that they do not, to any extent, limit the scope or practice of the invention.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% 3-(1substituted-4-piperazinyl)-1H-indazoles of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0-300 milligrams of the 3-(1-substituted-4-piperazinyl)-1H-indazoles of the present invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium or Sterotex, a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the 3-(1-substituted-4-piperazinyl)-1H-indazoles of the invention, but may be varied to be between 0.1 and about 50% of the weight thereof. The amount of the inventine compound present in such compositions is such that a suitable dosage will be obtained. Preferred compositions and preparations according to the present invention are prepared so that a parenteral dosage unit contains between 5.0 to 100 milligrams of the 3-(1-substituted-4-piperazinyl)-1H-indazoles of the invention.

The solutions or suspensions may also include the following adjuvants: a sterile diluent such as water for injection, saline solution, fixed oils, polyethylene glycols, glcerine, propylene glycol or other synthetic solvents, antibacterial agents such as benzyl alcohol or methyl paraben; antioxidants such as ascorbic acid or sodium bisulfite; chelating agents such as ethylene diaminetetraacetate acid buffers such as acetate, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade unless indicated otherwise.

EXAMPLE 1 a. 2-Bromobenzoic acid 2-phenylsulfonylhydrazide

To a solution of 2-bromobenzoic acid hydrazide (132 g) in pyridine (1.21), cooled to about 10° C. with an ice bath, was added benzenesulfonyl chloride (78.3 ml). After complete addition, the reaction was stirred at ambient temperature for 4 hours, and then poured into ice-HCl to precipitate a solid (135 g). The solid was recrystallized from isopropanol to yield 125 g of 2-bromobenzoic acid 2-phenylsulfonylhydrazide, m.p. 154°–156° C.

b. α-chloro-2-bromobenzaldehyde phenylsulfonylhydrazone

A mixture of 2-bromobenzene acid 2-phenylsulfonylhydrazide (125 g, 0.35 mol) of Example 1a and thionyl chloride (265 ml) was stirred and refluxed for 2 hours. The reaction was permitted to cool, and then it was poured into hexane. The resultant solid was collected to afford 124 g of α-chloro-2-bromobenzaldehyde phenylsulfonylhydrazone, m.p. 120°–122° C.

c. 1-[[(Phenylsulfonyl)hydrazono](2-bromophenyl)methyl]-4-methylpiperazine

To a stirred solution, under N$_2$, of the α-chloro-2-bromobenzaldehyde phenylsulfonylhydrazone (271.1 g. 0.72 mol) of Example 1b in tetrahydrofuran (THF) [2 l], was added, dropwise, N-methylpiperazine (159.7 g, 11.6 mol). The reaction was stirred at ambient temperature for 3 hours and then permitted to stand at ambient temperature for 16 hours. The reaction was chilled in an ice bath, and then filtered to remove the piperazine hydrochloride. The filtrate was concentrated to yield a gum. The gum was triturated with hot CH$_3$CN, the mixture was cooled in an ice bath and when cold it was filtered. The filtrate was then concentrated to afford 392.9 g of 1-[[(phenylsulfonyl)hydrazono](2-bromothenyl) methyl]-4-methylpiperazine.

d. 3-(4-Methyl-1-piperazinyl)-1-phenylsulfonyl-1H-indazole

A mixture of 1-[[(phenylsulfonyl)hydrazono](2-bromophenyl)methyl]-4-methylpiperazine (31.0 g, 0.08 mol), of Example 1c, copper-bronze (3.1 g), K$_2$CO$_3$ (11.5 g) and dimethylformamide (DMF) [500 ml] was stirred and refluxed for 1.5 hours. The reaction was poured into water and the aqueous suspension was stirred vigorously with ethyl acetate. The biphasic mixture was filtered through celite, and subsequently the layers were separated. The aqueous portion was extracted with another portion of ethyl acetate, and the combined extracts were washed (H$_2$O) and dried (MgSO$_4$). Concentration of the extract afforded a solid, which upon trituration with ether gave 19.7 g of a solid. The solid was recrystallized from isopropanol to afford 17.7 g (60%) of product, m.p. 158°–161° C. An analytical sample was obtained by another recrystallization from isopropanol (with charcoal treatment) to afford colorless crystals of the indazole, 3-(4-methyl-1-piperazinyl)-1-phenylsulfonyl-1H-indazole, m.p. 160°–161° C.

| ANALYSIS | | | |
|---|---|---|---|
| Calculated for C$_{18}$H$_{20}$N$_4$O$_2$S | 60.66% C | 5.66% H | 15.72% N |
| Found | 60.45% C | 5.62% H | 15.61% N | e. 4-[1-(Phenylsulfonyl)-1H-indazol-3-yl]-1-piperazinecarbonitrile

To a stirred mixture of 3-(4-methyl-1-piperazinyl)-1-phenylsulfonyl-1H-indazole (237 g, 0.67 mol) of Example 1d, K$_2$CO$_3$ (102 g, 0.74 mol) and dimethylsulfoxide (DMSO) [2000 ml] under N$_2$, was added cyanogen bromide (72 g, 0.68 mol) dissolved in DMSO (525 ml). The reaction was stirred at ambient temperature for 5.5 hours and was then poured into H$_2$O (7 l). The solid which precipitated from solution was collected by filtration and was washed well with H$_2$O affording 168 g (68%) of product. A 5.2 g sample was recrystallized twice from ethanol-H$_2$O yielding 4.0 g of 4-[1-(phenylsulfonyl)-1H-indazol-3-yl]-1-piperazinecarbonitrile, m.p. 178°–180° C.

| ANALYSIS | | | |
|---|---|---|---|
| Calculated for $C_{18}H_{17}N_5O_2S$ | 58.84% C | 4.66% H | 19.06% N |
| Found | 59.01% C | 4.63% H | 19.09% N | f. 1-Methyl-3-(1-piperazinyl)-1H-indazole

To a stirred suspension of 4-[1-(phenylsulfonyl)-1H-indazol-3-yl]-1-piperazinecarbonitrile of Example 1e (74.0 g, 0.20 mol) in anhydrous (THF) (750 ml) under $N_2$ was added, dropwise, sodium methoxide (400 ml; 25% sodium methoxide in methanol). The reaction was stirred at reflux for 2 hours and then for 16 hours at ambient temperature. The reaction was quenched by the dropwise addition of $H_2O$ (200 ml) which was then filtered. The filtrate was concentrated down to a residue which was triturated with ether. The ethereal triturant was filtered and the filtrate was then concentrated to afford an oil. The oil was diluted with $H_2O$ and the aqueous medium was extracted with ethyl acetate. The ethyl acetate extract was washed several times with $H_2O$, dried with $MgSO_4$ and concentrated to afford 43.5 g of an oil that contained a mixture of 4-(1-methyl-1-H-indazol-3-yl)-1-piperazinecarboximidic acid methyl ester (major) and 4-(1H-indazol-3-yl)-1-piperazinecarboximidic acid methyl ester (minor) piperazinylindazoles. To a stirred solution of the crude mixture of compounds (40.0 g, ca. 0.15 mol) in tetrahydrofuran (THF) [500 ml] under $N_2$ was added, dropwise, $LiAlH_4$ (300 ml; 2 eq of a 1M $LiAlH_4$ in THF). The reaction was stirred at reflux for 5 hours and was cooled in an ice bath. The excess $LIAlH_4$ was destroyed by the careful dropwise addition of $H_2O$ (300 ml). The resulting mixture was allowed to stand overnight (about 16 hours) and was then filtered through a coarse sintered glass funnel. The filter cake washed well with THF and the filtrate was concentrated to yield 27.2 g of an oil. The desired compound was separated from the crude oil by preparative HPLC (Water's Associates Prep LC/System 500, 2 silica gel columns, eluting with 20% diethylamine-ethyl acetate) to afford 12.0 g (28%) of an oil which solidified upon scratching. A 5.3 g sample was recrystallized twice from isopropyl ether to afford 3.0 g, (16%) of 1-methyl-3-(1-piperazinyl)-1H-indazole, m.p. 100°–102° C.

| ANALYSIS | | | |
|---|---|---|---|
| Calculated for $C_{12}H_{16}N_4$ | 66.64% C | 7.46% H | 25.90% N |
| Found | 66.85% C | 7.48% H | 25.75% N |

EXAMPLE 2

8-[4-[1-(1-Methyl-1H-indazol-3-yl)-4-piperazinyl]butyl-8-azaspiro[4,5]decane-7,9-dione fumarate A mixture of 1-methyl-3-(1-piperazinyl)-1H-indazole (2.4 g, 0.011 mol) 8-[4-(4-methylbenzenesulfonate)butyl-8-azaspiro[4,5]decane-7,9-dione (4.3 g, 0.011 mol), $Na_2CO_3$ (2.7 g) and DMF was stirred, under $N_2$ at 75° C. for 3 hours. The reaction was poured into $H_2O$ and the aqueous mixture was extracted with ether. The ether was washed ($H_2O$), dried ($MgSO_4$) and the solvent concentrated to afford 5.8 g of an oil. The oil was taken up in anhydrous ether and fumaric acid (1.5 g, 1 equiv.) was added. The mixture was stirred at ambient temperature for 16 hours and 5.1 g of the resultant fumarate salt was collected. Recrystallization from isopropanol-ether afforded 3.3 g (54%) of a solid, m.p. 167°–169° C. This material was combined with material from another run (0.1 g) and the combined sample was recrystallized from isopropanol-ether, ethyl acetate and again from isopropanol-ether to afford, after drying at 82° C. under vacuum, 2.0 g of 9-[4-[1-(1-methyl-1H-indazol-3-yl)-4-piperazinyl]butyl-8-azaspiro[4,5]decane-7,9-dione fumarate, m.p. 169°–171° C.

| ANALYSIS | | | |
|---|---|---|---|
| Calculated for $C_{25}H_{35}N_5O_2 \cdot C_4H_4O_4$ | 62.91% C | 7.10% H | 12.65% N |
| Found | 62.52% C | 7.11% H | 12.49% N |

EXAMPLE 3 a. 3-(1-Piperazinyl)-1H-indazole

A mixture of 4-(1H-indazol-3-yl)-1-piperazinecarbonitrile of Example 13 (8.0 g, 0.04 mol) and 25% $H_2SO_4$ (100 ml) was stirred at reflux for 4.5 hours. The reaction was cooled in an ice bath and made basic by the dropwise addition of 50% NaOH. The basic solution was extracted with ethyl acetate. The ethyl acetate was washed with $H_2O$, dried with $MgSO_4$ and concentrated to afford 5.2 g (73%) of the desired compound, as a solid. The solid was recrystallized twice from toluene to afford 3.0 g of 3-(1-piperazinyl)-1H-indazole, m.p. 153°–155° C.

| ANALYSIS | | | |
|---|---|---|---|
| Calculated for $C_{11}H_{14}N_4$ | 65.32% C | 6.98% H | 27.70% N |
| Found | 65.21% C | 6.99% H | 27.80% N | b. 8-[4-(4-Methylbenzenesulfonate]butyl-8-azaspiro[4.5]-decane-7,9-dione

To a solution of 8-(4-hydroxybutyl)-8-azaspiro[4.5]-decane-7,9-dione (8.6 g, 0.036 mol) in 90 ml of dry pyridine, cooled to 0° C. (ice, acetone), was added tosyl chloride (13.6 g, 0.056 mol). After the tosyl chloride had gone into solution, the flask was stored at 5° C. for 16 hours. The reaction mixture was poured onto 800 g of ice to yield a solid. The solid was washed with $H_2O$, dried (high vacuum at room temperature) to yield 124 g of a solid. The solid was dissolved in ether (500 ml.) and 1.2 g of decolorizing carbon added. The mixture was stirred at ambient temperature for 1 hour and then filtered through celite. The filtrate was then concentrated at room temperature to ca. 200 ml. Crystallization began to occur and the mixture was then cooled to about −50° C. with a dry ice-acetone bath. The resulting crystals were collected and dried to yield 10.3 g of a solid, m.p. 65°–68° C. of 8-[4-(4-methylbenzenesulfonate)butyl]-8-azaspiro[4.5]decane-7,9-dione hemifumarate.

c. 8-[4-[1-(1H-Indazol-3-yl)-4-piperazinyl]butyl-8-azaspiro[4.5]decane-7,9-dione A mixture of 3-(1-piperazinyl)-1H-indazole (4.6 g, 0.023 mol) of Example 3a, $K_2CO_3$ (3.3 g), DMF (75 ml) and 8-[4-(4-methylbenzenesulfonate)butyl]-8-azaspiro[4.5]decane-7,9-dione (8.9 g, 0.023 mol) of Example 3b was stirred and heated at 75° C., under $N_2$, for 3 hours. The reaction was poured into H₂O, and the aqueous mixture was extracted with ethyl acetate. The extract was washed (H₂O), dried (MgSO₄) and the solvent concentrated to afford an oil. The oil was dissolved in ethyl acetate (100 ml) and fumaric acid (2.7 g, 0.023 mol) was added. The mixture was heated to reflux and then was stirred at ambient temperature for 1 hour, to yield 6.4 g of a solid. The solid was recrystallized from isopropanol, ethanol and ether to afford 1.9 g (17%) of 8-[4-[1-(1H-indazol-3-yl)-4-piperazinyl]butyl-8-azaspiro[4.5]decane-7,9-dione hemifumarate, m.p. 198°–200° C.

| ANALYSIS | | | |
| --- | --- | --- | --- |
| Calculated for $C_{24}H_{33}N_5O_2 \cdot 0.5C_4H_4O_4$ | 64.84% C | 7.32% H | 14.54% N |
| Found | 64.23% C | 7.33% H | 14.39% N |

EXAMPLE 4 a. α-Chloro-5-bromo-2-chlorobenzaldehyde phenylsulfonylhydrazone

To a stirred mixture of 5-bromo-2-chlorobenzoic acid hydrazide (267.0 g, 0.99 mol) in dry pyridine (1.52) under N₂ and cooled to 0° C. was added, dropwise, benzenesulfonyl chloride (175.4 g, 0.99 mol) so that the temperature did not exceed 80° C. After complete addition, the reaction was stirred at ambient temperature for 3 hours. The reaction was allowed to stand for about 6.5 hours and then about ⅔ of the pyridine was removed in vacuo. The resultant liquid was poured into ice-HCl and the resultant gum was stirred until a solid formed. The solid was collected by filtration and was washed well with H₂O. The compound was dried and weighed to yield 599 g of a solid. The solid was recrystallized twice from isopropanol to afford 305 g (79%) of a solid which appeared pure by thin layer chromatography (TLC). A 4.0 g sample was recrystallized two more times from isopropanol (utilizing decolorizing carbon) to yield 1.8 g (36%) of α-chloro-5-bromo-2-chlorobenzaldehyde-2-phenylsulfonylhydrazone, m.p. 149°–151° C.

| ANALYSIS | | | |
| --- | --- | --- | --- |
| Calculated for $C_{13}H_{10}BrClN_2O_3S$ | 40.07% C | 2.59% H | 7.19% N |
| Found | 39.92% C | 2.42% H | 7.24% N | b. 1-{[Phenylsulfonyl)hydrazono](5-bromo-2-chlorophenyl)methyl}-4-methylpiperazine To a stirred mixture of α-chloro-5-bromo-2-chlorobenzaldehyde phenylsulfonylhydrazone of Example 4a (268.0 g, 0.66 mol) in tetrahydrofuran (THF) (1.3 l) cooled to 4° C. under N₂ was added, dropwise, 1-methylpiperazine (145.0 g, 1.44 mol) over the course of 45 minutes. After complete addition, the reaction was stirred at ambient temperature for 16 hours. The mixture was filtered and the filter cake was washed well with THF. The filtrate was concentrated to afford 351.0 g of a paste. The paste was triturated with hot CH₃CN and allowed to cool. This was then filtered and the CH₃CN filtrate was concentrated to yield 182.0 g (59%) of a solid. A 5.0 g sample was purified by preparative high pressure liquid chromatography (HPLC) (Water's Associates Prep. LC/System 500; 2 silica gel columns; eluting with 2% diethylamine-ethyl acetate) to yield 3.2 g (38%) of a solid. The solid was recrystallized from isopropanol to yield 2.0 g (24%) of 1-{[phenylsulfonyl)hydrazono](5-bromo-2-chlorophenyl)methyl}-4-methylpiperazine, m.p. 133°–135° C.

| ANALYSIS | | | |
| --- | --- | --- | --- |
| Calculated for $C_{18}H_{20}BrClN_4O_2S$ | 45.82% C | 4.28% H | 11.88% N |
| Found | 45.68% C | 4.20% H | 11.82% N | c. 5-Bromo-3-(4-methyl-1-piperazinyl)-1-phenylsulfonyl-1H-indazole

A mixture of 1-{[(phenylsulfonyl)hydrazono](5-bromo-2-chlorophenyl)methyl}-4-methylpiperazine (176.0 g, 0.37 mol) of Example 4b, potassium carbonate (61.0 g, 0.44 mol), copper-bronze (14.0 g) and dimethylformamide (DMF) (2.02 l) was stirred at reflux for 4 hours. The reaction was allowed to stand overnight (about 16 hours) and was then poured into H₂O (4 l). Ethyl acetate (3 l) was added and the biphasic mixture was stirred vigorously for 5 minutes and was then filtered through celite. The layers were separated and the aqueous phase was extracted again with ethyl acetate. The combined ethyl acetate extract was washed with H₂O, dried with MgSO₄ and concentrated to afford 141.0 g of an oil. The oil was triturated with ether and filtered to yield 51.0 g of a solid as the desired product. The filtrate was then concentrated to afford 53.0 g of an oil. An 18.0 g sample of the oil was purified by preparative HPLC (Water's Associates Prep. LC/System 500, utilizing 2 silica gel columns and 4% methanol-CH₂Cl₂ as eluent) affording 11.0 g of a solid. A 4.5 g sample was recrystallized from isopropanol to afford 3.0 g (26%) of 5-bromo-3-(4-methyl-1-piperazinyl)-1-phenylsulfonyl-1H-indazole, m.p. 135°–137° C.

| ANALYSIS | | | |
| --- | --- | --- | --- |
| Calculated for $C_{18}H_{19}BrN_4O_2S$ | 49.66% C | 4.41% H | 12.87% N |
| Found | 49.87% C | 4.36% H | 12.84% N | d. 5-Bromo-3-(4-methyl-1-piperazinyl)-1H-indazole

To a stirred solution, under N₂, 5-bromo-3-(4-methyl-1-piperazinyl)-1-phenylsulfonyl-1H-indazole (4.4 g, 0.01 mol) of Example 4c in THF (70 ml), was added, dropwise, lithium aluminum hydride [20 ml of a 1M solution in tetrahydrofuran (THF)]. The reaction was then stirred for 6 hours at reflux. The reaction was cooled in an ice bath, water was added cautiously and then the reaction was filtered. The filter cake was washed with THF and then methanol, and the filtrate was concentrated to yield 5-bromo-3-(4-methyl-1-piperazinyl)-1H-indazole.

EXAMPLE 5 a. 2-Bromo-5-methoxybenzoic acid 2-phenylsulfonyl hydrazide

To a stirred mixture of 2-bromo-5-methoxybenzoic acid hydrazide (397 g, 1.62 mol) in dry pyridine (2.25 l) under N₂ and cooled to 0° C. was added, dropwise, benzenesulfonyl chloride (290 g, 1.64 mol). After complete addition the reaction was stirred at ambient temperature for 3 hours. Most of the pyridine was removed and the resultant liquid was poured into ice-HCl. The solid which formed was collected and washed well with H₂O and dried to afford a solid. The compound was recrystallized from isopropanol to afford 560 g of a solid. A 4.0 g sample was recrystallized again from isopropanol to yield 3.5 g (75%) of 2-bromo-5-methoxybenzoic acid 2-phenylsulfonyl hydrazide, m.p. 150°–152° C.

| ANALYSIS | | | |
|---|---|---|---|
| Calculated for $C_{14}H_{13}BrN_2O_4S$ | 43.65% C | 3.41% H | 7.27% N |
| Found | 43.48% C | 3.28% H | 7.26% N | b. α-Chloro-2-bromo-5-methoxybenzaldehyde phenylsulfonylhydrazone

A mixture of 2-bromo-5-methoxybenzoic acid 2-phenylsulfonylhydrazide (556.0 g, 144 mol) and thionyl chloride (1200 ml) was stirred at reflux for 24 hours. About half of the thionyl chloride was distilled from the reaction and the reaction was then allowed to cool to room temperature. Hexane was added to the stirred mixture and the resultant solid was collected and washed well with hexane. The solid was dried and weighed affording 579.0 g of a solid. The solid was recrystallized from toluene to afford 495.0 g. A 4.0 g sample was dissolved in ethyl acetate (100 ml) and decolorizing carbon (110 mg) was added. The mixture was heated at a gentle reflux for 10 minutes and then filtered through celite. The ethyl acetate was removed in vacuo yielding 3.4 g of a solid. This solid was recrystallized once again from toluene to afford 2.5 g of α-chloro-2-bromo-5-methoxybenzaldehyde phenylsulfonylhydrazone, m.p. 104°–106° C.

| ANALYSIS | | | |
|---|---|---|---|
| Calculated for $C_{14}H_{12}BrClN_2O_3S$ | 41.66% C | 3.00% H | 6.94% N |
| Found | 41.68% C | 2.89% H | 6.99% N | c. 1-{[(Phenylsulfonyl)hydrazono](2-bromo-5-methoxyphenyl)methyl}-4-methylpiperazine To a stirred solution of α-chloro-2-bromo-5-methoxybenzaldehyde-phenylsulfonylhydrazone (490.0 g, 1.21 mol) of Example 5b dissolved in tetrahydrofuran [THF] (2.5 l) under N₂ and chilled to 10° C. was added, dropwise, 1-methylpiperazine (267.0 g, 2.67 mol). After total addition, the reaction was stirred at ambient temperature for 2.5 hours. The mixture was cooled in an ice bath and then filtered. The filter cake was washed well with cold THF. The filtrate was concentrated to afford a paste. This was triturated with CH₃CN and filtered and the filtrate concentrated to afford 237.0 g of an oil. The filter cake from the first filtering process with THF was diluted with CH₂Cl₂ (2 l) and stirred for 5 minutes then filtered. This filter cake was washed well with CH₂Cl₂ and the filtrate was concentrated to afford a gum. This gum was combined with the oil (237.0 g) and was triturated with ether producing a solid which was collected, dried and weighed to afford 335 g of the target compound. A 5.0 g sample was dissolved in ethyl acetate (100 ml) and treated with decolorizing carbon (150 mg). The mixture was stirred at a gentle reflux for 10 minutes and then filtered. The ethyl acetate filtrate was concentrated to afford 4.8 g of a solid. The compound was recrystallized from isopropanol to afford 4.0 g (47%) of 1-{[(phenylsulfonyl)hydrazono](2-bromo-5-methoxyphenyl)methyl}-4-methylpiperazine, m.p. 141°–145° C.

| ANALYSIS: | | | |
|---|---|---|---|
| Calculated for $C_{19}H_{23}BrN_4O_3S$: | 48.82% C | 4.97% H | 11.99% N |
| Found: | 48.78% C | 4.86% H | 11.96% N | d. 3-(4-Methyl-1-piperazinyl)-5-methoxy-1-phenylsulfonyl-1H-indazole

A mixture of 1-{[(phenylsulfonyl)hydrazono](2-bromo-5-methoxyphenyl)methyl}-4-methylpiperazine (329.0 g, 0.70 mol) of Example 5c, K₂CO₃ (117.0 g, 0.85 mol), copper-bronze (24.0 g) and dimethylformamide (DMF) (4.0 l) was stirred at reflux under N₂ for 4 hours. The mixture was allowed to stand overnight and was then poured into H₂O. Ethyl acetate (3 l) was added and the mixture was stirred vigorously for 5 minutes. After filtering through celite the biphasic mixture was separated and the H₂O layer was extracted again with ethyl acetate. The combined organic extract was washed with brine, dried with MgSO₄ and concentrated to afford 29.8 g of a solid. This solid was triturated with ether to afford 137.3 g (52%) of a solid. A 5.0 g sample was purified by preparative HPLC (Water's Associates Prep. LC/System 500, 2 silica gel columns, eluting with 4% diethylamine-ethyl acetate) to afford 4.3 g of a solid. The solid was treated with decolorizing carbon in CHCl₃ and subsequently recrystallized from isopropanol to afford 3.7 g (38%) of 3-(4-methyl-1-piperazinyl)-5-methoxy-1-phenylsulfonyl-1H-indazole, m.p. 165°–167° C.

| ANALYSIS: | | | |
|---|---|---|---|
| Calculated for $C_{19}H_{12}N_4O_3S$: | 59.05% C | 5.75% H | 14.50% N |
| Found: | 59.02% C | 5.71% H | 14.55% N |

EXAMPLE 6

1-Acetyl-5-methoxy-3-(4-methyl-1-piperazinyl)-1H-indazole Hydrochloride

A mixture of 3-(4-methyl-1-piperazinyl)-1-phenylsulfonyl-1H-indazole (23.5 g, 0.09 mol) was stirred at reflux for 5 hours and was then allowed to stand overnight (about 16 hours). The reaction was filtered and the filter cake was washed well with THF. The filtrate was concentrated to yield a residue which was diluted with ethyl acetate. The solution was stirred for 5 minutes and then H₂O was added. The phases were separated and the H₂O layer was extracted with additional ethyl acetate. The ethyl acetate extract was washed with H₂O, dried with MgSO₄ and concentrated to afford 16.0 g cf a gum. The gum was purified by preparative HPLC (Water's Associates Prep. LC/System 500, utilizing 2 silica gel columns and 20% MeOH-CH₂Cl₂ as eluent). A 6.0 g sample was dissolved in anhydrous ether and then methanol (minimal amount) and ethereal HCl was added to precipitate 6.7 g of the hydrochloride salt. The salt was recrystallized from ethanol to yield 5.0 g (26%) of 1-acetyl-5-methoxy-3-(4- methyl-1-piperazinyl)-1H-indazole hydrochloride, m.p. 262°-254° C.

ANALYSIS:

| | | | |
|---|---|---|---|
| Calculated for $C_{15}H_{20}N_4O_2 \cdot HCl$: | 55.46% C | 6.53% H | 17.25% N |
| Found: | 55.30% C | 6.36% H | 17.11% N |

EXAMPLE 7

5-Methoxy-3-(4-methyl-1-piperazinyl)-1H-indazole

A mixture of 3-(4-methyl-1-piperazinyl)-5-methoxy-1-phenylsulfonyl-1H-indazole (23.5 g, 0.06 mol) of Example 5d, THF (230 ml) and milled KOH (5.3 g, 0.09 mol) was stirred at reflux for 5 hours and was then allowed to stand for 16 hours. The reaction was filtered and the filter cake was washed well with THF. The filtrate was concentrated down to a residue which was partitioned between $H_2O$ and ethyl acetate. The ethyl acetate extract was washed with $H_2O$, dried with $MgSO_4$ and concentrated to afford 16.0 g of a gum. The gum was purified by preparative HPLC (Water's Associates Prep. LC/System 500, utilizing 2 silica gel columns and 20% methanol-$CH_2Cl_2$ as eluent) affording 7.0 g (47%) of a solid. Two consecutive recrystallizations of the solid from toluene yielded 4.4 g of 5-methoxy-3-(4-methyl-1-piperazinyl)-1H-indazole, m.p. 158°-160° C.

ANALYSIS:

| | | | |
|---|---|---|---|
| Calculated for $C_{13}H_{18}N_4O$: | 63.38% C | 7.38% H | 22.75% N |
| Found: | 63.27% C | 7.35% H | 22.71% N |

EXAMPLE 8

1-Benzoyl-5-methoxy-3-(4-methyl-1-piperazinyl)-1H-indazole hydrochloride

A mixture of 5-methoxy-3-(4-methyl-1-piperazinyl)-1H-indazole (3.0 g, 0.0122 mol) of Example 7 and benzoyl chloride (20 ml) was warmed on a steam bath under $N_2$ for 2 hours. The cooled mixture was diluted with ether and was then filtered. The resultant solid was washed well with ether and dried to afford 4.0 g (85%) of a solid. The solid was recrystallized twice from ethanol to afford 2.4 g (52%) of 1-benzoyl-5-methoxy-3-(4-methyl-1-piperazinyl)-1H-indazole hydrochloride, m.p. 253°-255° C.

ANALYSIS:

| | | | |
|---|---|---|---|
| Calculated for $C_{20}H_{22}N_4O_2 \cdot HCl$: | 62.08% C | 6.00% H | 14.48% N |
| Found: | 61.63% C | 5.89% H | 14.41% N |

EXAMPLE 9

4-(5-methoxy-1-phenylsulfonyl-1H-indazol-3-yl)-1-piperazinecarbonitrile

To a stirred mixture of 3-(4-methyl-1-piperazinyl)-5-methoxy-1-phenylsulfonyl-1H-indazole (55.0 g, 0.14 mol) of Example 5d, potassium carbonate (22.0 g, 0.16 mol) and dimethylsulfoxide (DMSO) [500 ml] under $N_2$ was added dropwise, cyanogen bromide (16.0 g, 0.15 mol) dissolved in DMSO (125 ml). The reaction was stirred at room temperature for 4 hours and was then poured into $H_2O$ (2.5 l). The solid which formed was collected and washed well with $H_2O$. The solid was dried and weighed to yield 41.0 g. A 5.0 sample was recrystallized twice from ethanol (utilizing decolorizing carbon) to afford 3.5 g (50%) of 4-(5-methoxy-1-phenyl-sulfonyl-1H-indazol-3-yl)-1-piperazinecarbonitrile. m.p. 171°-173° C.

ANALYSIS:

| | | | |
|---|---|---|---|
| Calculated for $C_{19}H_{19}N_5O_3S$: | 57.43% C | 4.83% H | 17.63% N |
| Found: | 57.26% C | 4.77% H | 17.52% N |

EXAMPLE 10

5-Methoxy-3-(1-piperazinyl)-1H-indazole

To a stirred mixture of 4-[5-methoxy-1-phenylsulfonyl-1H-indazol-3-yl]-1-piperazinecarbonitrile (9.5 g, 0.0239 mol) in THF (150 ml) under $N_2$ was added, dropwise, lithium aluminum [50 ml (2.1 eq) of a 1M $LiAlH_4$ solution in THF]. After complete addition the reaction was warmed to reflux and stirred for 3 hours. To the cooled reaction was added carefully, $H_2O$ (15 ml) to destroy the excess $LiAlH_4$. The mixture was allowed to stand overnight. The reaction mixture was filtered through a coarse sintered glass funnel. The resultant cake was washed well with THF and the THF filtrate was concentrated to afford 6.0 g, of a residue. The residue was triturated with ether and $H_2O$ and the resultant solid was collected and dried to afford 4.5 g of 5-methoxy-3-(1-piperazinyl)-1H-indazole, m.p. 163°-169° C.

EXAMPLE 11

5-Methoxy-3-{4-[3-(2-methylindol-3-yl)propyl]-1-piperazinyl}-1H-indazole hemifumarate A mixture of 5-methoxy-3-(1-piperazinyl)-1H-indazole (4.0 g, 0.0172 mol), potassium carbonate (3.0 g, 0.0217 mol), 3-(3-phenylsulfonyloxypropyl)-2-methylindole (6.2 g, 0.0189 mol) and dimethylformamide (DMF) [75 ml] was stirred at 75° C. for 3.5 hours. The cooled reaction was poured into $H_2O$ and the aqueous mixture was extracted with ethyl acetate. The organic extract was washed with $H_2O$, dried with $MgSO_4$ and concentrated to afford 8.3 g of an oil. The sample was purified by preparative HPLC (Water's Associates Prep. LC/System 500, utilizing 2 silica gel columns and 6% methanol $CH_2Cl_2$ as solvent) to yield 5.2 g of a solid. The solid was taken up in ethyl acetate (100 ml) and fumaric acid (1.6 g) was added. The mixture was stirred for 20 minutes at a mild reflux and was allowed to stand at room temperature overnight (about 16 hours) under $N_2$. The resultant solid was collected and dried to afford 5.0 g (63%) of the target compound as a hemifumarate. The sample was triturated with hot ethanol and filtered hot yielding 4.0 g of a solid. The solid was recrystallized from $CH_3CN$, and then from DMF-$H_2O$ to provide 2.4 g (30%) of 5-methoxy-3-{4-[3-(2-methylindol-3-yl)propyl]-1-piperazinyl}}-1H-indazole hemifumarate, m.p. 145°-147° C.

ANALYSIS:

| | | | |
|---|---|---|---|
| Calculated for $C_{26}H_{31}N_5O_3$: | 67.64% C | 6.78% H | 15.17% N |
| Found: | 67.29% C | 6.81% H | 15.10% N |

EXAMPLE 12

5-Methoxy-3-{4-[3-(2-methylindol-3-yl)propyl]-1-piperazinyl}-1H-indazole hemifumarate To a stirred mixture of 5-methoxy-3-(1-piperazinyl)-1H-indazole (4.0 g, 0.0172 mol) of Example 10 sodium bicarbonate (1.75 g, 0.0206 mol), potassium iodide (2.50 mg) and dimethylformamide (DMF), was added, dropwise, 1-(3-chloropropyl)-1,3-dihydro-2H-benzimidazol-2-one (4.0 g, 0.0189 mol) dissolved in DMF (45 ml). The reaction was heated to 80° C. and stirred for 7 hours and was then allowed to stand overnight (about 16 hours). The reaction was poured into $H_2O$ and the aqueous mixture was extracted with ethyl acetate. The organic extract was washed with $H_2O$, dried with $MgSO_4$ and concentrated to yield 8.5 g of an oil. The oil was purified by preparative HPLC (Water's Associates Prep. LC/System 500, utilizing 2 silica gel columns and eluting with 10% methanol-$CH_2Cl_2$) affording 3.0 g of a solid. The solid was dissolved in ethyl acetate and fumaric acid (0.95 g) was added. The mixture was stirred at reflux for 15 minutes and at ambient temperature for 30 minutes. The resultant solid was collected and dried to afford 4.2 g (53%) of product. The solid was recrystallized twice from ethanol-ether to yield 2.4 g of 5-methoxy-3-{4-[3-(3-dihydro-2-oxo-2H-benzimidazol-1-yl)propyl]-1-piperazinyl}-1H-indazole hemifumarate, m.p. 195°–197° C.

| ANALYSIS: | | | |
|---|---|---|---|
| Calculated for $C_{22}H_{26}N_6O_2.0.5C_4H_4O_4$: | 62.04% C | 6.09% H | 18.09% N |
| Found: | 61.94% C | 6.05% H | 17.95% N |

EXAMPLE 13

3-(4-Methyl-1-piperazinyl)-1H-indazole

A stirred mixture of 3-(4-methyl-1-piperazinyl)-1-phenylsulfonyl-1H-indazole (13.5 g, 0.038 mol) of Example 1d, methanol (150 ml) and 25% sodium methoxide in methanol (15.3 ml) was stirred and refluxed for 2.5 hours. The reaction was concentrated to about 1/10th its volume, and water was added to the mixture. The solution was extracted with $CH_2Cl_2$, the extract was washed ($H_2O$), dried ($MgSO_4$) and the solvent was concentrated to afford 6.6 g of a solid. Two recrystallizations from toluene-hexane afforded 4.3 g (52%) of 3-(4-methyl-1-piperazinyl)-1H-indazole, m.p. 111°–113° C.

| ANALYSIS: | | | |
|---|---|---|---|
| Calculated for $C_{12}H_{16}N_4$: | 66.64% C | 7.46% H | 25.91% N |
| Found: | 66.83% C | 7.42% H | 25.69% N |

EXAMPLE 14

4-(1H-indazol-3-yl)-1-piperazinecarbonitrile

To a stirred mixture of BrCN (5.3 g, 0.05 mol), $K_2CO_3$ (7.1 g) and dimethylsulfoxide (DMSO) (40 ml) was added, dropwise, 3-(4-methyl-1-piperazinyl)-1H-indazole (11.0 g, 0.051 mol) of Example 12 dissolved in DMSO (60 ml). The reaction was stirred at ambient temperature for 1 hour and then it was poured into $H_2O$. The aqueous suspension was extracted with ethyl acetate, the ethyl acetate was washed ($H_2O$), dried ($MgSO_4$) and concentrated to afford 7.8 g (76%) of a solid. This sample was combined with another and recrystallized twice from toluene, to afford 4-(1H-indazol-3-yl)-1-piperazinecarbonitrile, m.p. 120°–122° C.

| ANALYSIS: | | |
|---|---|---|
| Calculated for $C_{12}H_{13}N_5$: | 63.42% C | 5.76% H |
| Found: | 63.04% C | 5.84% H |

EXAMPLE 15

1-Acetyl-3-(4-methyl-1-piperazinyl)-1H-indazole

A mixture of 3-(4-methyl-1-piperazinyl)-1H-indazole (5.0 g, 0.023 mol) of Example 13 and acetic anhydride (50 ml) under $N_2$ was stirred at reflux for 1.5 hours. Most of the acetic anhydride was removed in vacuo and the resultant oil was diluted with $H_2O$. The solution was made basic by the dropwise addition of $NH_4OH$ and the precipitant which formed was collected and dried to yield 5.6 g of a solid. The compound was converted to the HCl salt by dissolving the solid in anhydrous ether and methanol (minimal amount) and adding ethereal HCl to afford 4.0 g of a solid. The solid was converted to 3.0 g of the free base, and was subsequently recrystallized from ethyl acetate at 4° C. to afford 2.2 g of 1-acetyl-3-(4-methyl-1-piperazinyl)-1H-indazole, m.p. 106°–108° C.

| ANALYSIS: | | | |
|---|---|---|---|
| Calculated for $C_{14}H_{18}N_4O$: | 65.09% C | 7.02% H | 21.69% N |
| Found: | 65.11% C | 6.95% H | 21.66% N |

EXAMPLE 16

1-Benzoyl-3-(4-methyl-1-piperazinyl)-1H-indazole

A mixture of 3-(4-methyl-1-piperazinyl)-1H-indazole (3.0 g, 0.014 mol) of Example 13 and benzoyl chloride (5 ml) was heated on a steam bath for 2 hours. After cooling, ether was added and 5.0 g of a hydrochloride salt was collected. The salt, along with a 2.0 g sample from a previous run, was suspended in $H_2O$, and $NH_4OH$ added until the mixture was basic. The aqueous suspension was extracted with $CH_2Cl_2$, the extract was washed ($H_2O$), dried ($K_2CO_3$) and was concentrated to afford 6.1 g of the benzoylated indazole. Recrystallization (twice) from isopropyl ether afforded 2.3 g (27%) of 1-benzoyl-3-(4-methyl-1-piperazinyl)-1H-indazole, m.p. 104°–106° C.

| ANALYSIS: | | | |
|---|---|---|---|
| Calculated for $C_{19}H_{20}N_4O$: | 71.22% C | 6.29% H | 17.49% N |
| Found: | 71.00% C | 6.29% H | 17.59% N |

EXAMPLE 17

1-Ethyl-3-(4-methyl-1-piperazinyl)-1H-indazole hydrochloride

To a stirred suspension of NaH (1.14 g, 0.024 mol; 50% oil dispersion) in DMF (50 ml) was added, dropwise, 3-(4-methyl-1-piperazinyl)-1H-indazole (4.0 g, 0.019 mol) of Example 13 in DMF (20 ml). The reaction was stirred at ambient temperature for 45 minutes, then ethyl bromide (2.59 g, 0.024 mol) in DMF (10 ml) was added dropwise. The reaction was allowed to stir at ambient temperature under $N_2$ for 17 hours and was then poured into $H_2O$. The aqueous mixture was extracted five times with 100 ml portions of ethyl acetate. The ethyl acetate extracts were combined and washed with $H_2O$, dried with $MgSO_4$ and concentrated to afford 5.0 g of an oil. The oil was taken up in anhydrous ether and ethereal HCl was added to precipitate 4.3 g (83%) of the indazole as the HCl salt. The compound was recrystallized twice from isopropanol-ether to afford 2.2 g of 1-ethyl-3-(4-methyl-1-piperazinyl)-1H-indazole hydrochloride, m.p. 201°–203° C.

| ANALYSIS: | | | |
|---|---|---|---|
| Calculated for $C_{14}H_{20}N_4$.HCl: | 59.87% C | 7.55% H | 19.95% N |
| Found: | 59.33% C | 7.31% H | 19.75% N |

EXAMPLE 18

1-Methyl-3-(4-methyl-1-piperazinyl)-1H-indazole hydrochloride

To a stirred suspension of NaH (0.75 g, 0.0155 mol; 50% oil dispersion) in DMF (20 ml) under $N_2$ was added, dropwise, 3-(4-methyl-1-piperazinyl)-1-indazole (2.8 g, 0.0129 mol) of Example 13 dissolved in DMF (30 ml). The mixture was stirred at ambient temperature for 1.5 hours. The reaction was then cooled in an ice-salt bath and iodomethane (2.0 g, 0.0142 mol) in DMF (10 ml) was added dropwise so that the temperature did not exceed 8° C. After complete addition the ice-salt bath was removed and the reaction was allowed to stir at ambient temperature for 3 hours. The reaction mixture was poured into $H_2O$ and the aqueous mixture was extracted with ethyl acetate. The ethyl acetate was washed with $H_2O$, dried with $MgSO_4$ and concentrated to afford 2.7 g of a liquid. The liquid was taken up in ether and methanol (minimal amount), and ethereal HCl was added to precipitate 2.1 g of the HCl salt (65%). This was combined with an additional sample to give a total of 4.0 g of the compound, which was recrystallized twice from ethanol to afford 2.2 g of a solid. The compound appeared to have occluded $H_2O$ (by NMR analysis), and this was effectively removed by drying under high vacuum at 110° C. for 17 hours, to afford 2.0 g of 1-methyl-3-(4-methyl-1-piperazinyl)-1H-indazole hydrochloride, m.p. 228°–230° C.

| ANALYSIS | | | |
|---|---|---|---|
| Calculated for $C_{13}H_{18}N_4$.HCl | 58.52% C | 7.19% H | 21.00% N |
| Found | 57.99% C | 7.18% H | 20.95% N |

EXAMPLE 19

1-Cyclopropylmethyl-3-(4-methyl-1-piperazinyl)-1H-indazole

To a stirred suspension of NaH (1.4 g, 0.0342 mol), 50% oil dispersion) and DMF (40 ml) under $N_2$ was added, dropwise, 3-(4-methyl-1-piperazinyl)-1H-indazole of Example 13 (6.16 g, 0.0285 mol) dissolved in DMF (40 ml). The mixture was stirred at ambient temperature for 1.5 hours and then (bromomethyl)cyclopropane (5.0 g, 0.0371 mol) in DMF (20 ml) was added, dropwise, to the reaction over the course of 10 minutes. The reaction was allowed to stir for 2.5 hours and was then poured into $H_2O$. The aqueous mixture was extracted with ethyl acetate. The ethyl acetate was washed with $H_2O$, dried with $MgSO_4$ and then concentrated to afford 6.8 g of an oil. The oil was triturated with $H_2O$ and the resulting solid was collected by filtration, to yield 5.0 g (65%) of TLC-pure compound. A 4.2 g sample of the solid was purified by preparative HPLC (Water's Associates Prep. LC/System 500, 2 silica gel columns, eluting with 3% diethylamine-ethyl acetate) to afford 2.9 g of 1-cyclopropylmethyl-3-(4-methyl-1-piperazinyl)-1H-indazole, m.p. 68°–70° C.

| ANALYSIS | | | |
|---|---|---|---|
| Calculated for $C_{16}H_{22}N_4$ | 71.06% C | 8.22% H | 20.72% N |
| Found | 70.69% C | 8.21% H | 20.58% N |

EXAMPLE 20 a. α-Chloro-2,5-dichlorobenzaldehyde phenylsulfonylhydrazone

A mixture of the 2,5-dichlorobenzoic hydrazide (246 g, 0.71 mol) and thionyl chloride (600 ml) was stirred at reflux for 3 hours. The solution was allowed to cool and was poured into hexane. The solid which precipitated was collected by filtration and washed well with hexane. The product was dried and weighed to afford 234 g (91%) of a solid, m.p. 133°–135° C. The compound was recrystallized from toluene and washed with hexane. After drying the solid in a vacuum oven overnight at room temperature, 222 g (86%yield) of α-chloro-2,5-dichlorobenzaldehyde phenylsulfonylhydrazone, m.p. 133°–135° C., was obtained.

b. 3-(4-methyl-1-piperazinyl)-5-chloro-1-phenylsulfonyl-1H-indazole

To a stirred solution of α-chloro-2,5-dichlorobenzaldehyde phenyl sulfonylhydrazone (222.0 g, 0.61 mol) of Example 20 in tetrahydrofuran (THF) (1.2 l), under $N_2$ was added, dropwise, 1-methylpiperazine (135.0 g, 1.34 mol) over the course of one hour. After total addition, the reaction was allowed to stir at ambient temperature for 22 hours. The mixture was cooled in an ice bath and filtered. The filter cake was washed well with THF and the filtrate concentrated to afford 142.0 g (55%) of 1-{[(phenylsulfonyl)hydrazone](2,5-dichlorophenyl)methyl}-4-methylpiperazine. A mixture of 1-{[(phenylsulfonyl)hydrazone](2,5-dichlorophenyl)methyl}-4-methylpiperazine (142.0 g, 0.33 mol), $K_2CO_3$ (55.0 g, 0.40 mol), copper bronze (10.0 g) and DMF (2.1 l) was stirred a reflux for 5 hours and was then allowed to stand overnight (about 16 hours). The reaction was poured into $H_2O$ (4 l) and ethyl acetate (2 l) was added. The biphasic mixture was stirred vigorously and then filtered through a bed of celite. The two phases were separated and the $H_2O$ layer was extracted again with ethyl acetate. The combined ethyl acetate extract was washed with $H_2O$, dried with $MgSO_4$ and concentrated to afford 80.0 g of an oil. The oil was triturated with ether and the resultant solid was collected and dried to afford 27.0 g (21%) of product. The filtrate was concentrated to an oil which was purified by preparative HPLC (Water's Prep. LC/System 500A, 2 silica gel columns, eluting with 5% methanol-$CH_2Cl_2$) yielding 27.0 g (21%) of a solid. The two samples were combined and an analytically pure sample was obtained by two recrystallizations of a 4.0 g sample from isopropanol (utilizing decoloring carbon) to yield 2.5 g (18%) of 3-(4-methyl-1-piperazinyl)-5-chloro-1-phenylsulfonyl-1H-indazole, m.p. 145°–147° C.

| ANALYSIS | | | |
|---|---|---|---|
| Calculated for $C_{18}H_{19}ClN_4O_2S$ | 55.31% C | 4.91% H | 14.34% N |
| Found | 55.19% C | 4.91% H | 14.34% N | c. 5-Chloro-3-(4-methyl-1-piperazinyl)-1H-indazole

A mixture of 3-(4-methyl-1-piperazinyl)-5-chloro-1-phenylsulfonyl-1H-indazole (23.0 g, 0.06 mol) of Example 20b, milled KOH (95.3 g, 0.09 mol) and tetrahydrofuran (THF) [230 ml] was stirred at reflux under $N_2$ for 5 hours. The reaction was cooled to room temperature, filtered and the filter cake was washed well with THF (4 times with 25 ml portions). The filtrate was concerned to afford 18.9 g of a residue, which was partitioned between toluene and $H_2O$ resulting in a suspended solid. The mixture was filtered and a solid was collected and dried to afford 6.7 g (45%). The two phases of the filtrate were separated and the aqueous layer was extracted again with toluene. The combined organic extract was washed with $H_2O$, dried with $MgSO_4$ and concentrated to afford 10.0 g of an oil, which upon trituration with hexane produced a solid. The solid was collected by filtration and dried to yield 5.3 g (38%). The two samples that were obtained were combined to yield a total of 12.0 g. A 4.0 g sample was dissolved in ethyl acetate (100 ml) and decolorizing carbon (100 mg) was added. The mixture was heated on a steam bath for 15 minutes and filtered through a bed of celite. The filtrate was concentrated to afford 3.4 g of a solid which was recrystallized from toluene to afford 2.5 g of 5-chloro-3-(4-methyl-1-piperazinyl)-1H-indazole, m.p. 172°–174° C.

| ANALYSIS | | | |
|---|---|---|---|
| Calculated for $C_{12}H_{15}ClN_4$ | 57.47% C | 6.04% H | 23.35% N |
| Found | 57.35% C | 5.99% H | 21.95% N |

EXAMPLE 21

1-Benzoyl-5-chloro-3-(4-methyl-1-piperazinyl)-1H-indazole

A mixture of 5-chloro-3-(4-methyl-1-piperazinyl)-1H-indazole (4.0 g, 0.016 mol) of Example 20c and benzoyl chloride (15 ml) was heated on a steam bath for 4 hours. The cooled reaction was diluted with ether (100 ml) and allowed to sit overnight. A solid was collected and dried to afford 7.0 g. The solid was converted to the free base by suspending it in $H_2O$ (100 ml) and adding $NH_4OH$. The aqueous mixture was extracted with $CH_2Cl_2$ and the organic phase was washed with $H_2O$, dried with $MgSO_4$ and concentrated to afford 4.8 g of a solid. A 4.0 g sample was purified by HPLC (Water's Prep. LC/System 500A, 2 silica gel columns, eluting with 2% diethylamine-ethyl acetate) to afford 3.4 g (72%). A single recrystallization from isopropanol afforded 2.5 g (53%) of 1-benzoyl-5-chloro-3-(4-methyl-1-piperazinyl)-1H-indazole, m.p. 105°–107° C.

| ANALYSIS | | | |
|---|---|---|---|
| Calculated for $C_{19}H_{19}ClN_4O$ | 64.30% C | 5.41% H | 15.79% N |
| Found | 64.47% C | 5.45% H | 15.80% N |

EXAMPLE 22

3-{4-[3-(1,3-dihydro-2-oxo-2H-benzimidazol-1-yl)propyl]-1-piperazinyl}-1H-indazole To a stirred mixture of 3-(1-piperazinyl)-1H-indazole (5.0 g, 0.0247 mol) of Example 22, $NaHCO_3$ (2.3 g, 0.027 mol), KI (230 mg) and dimethylformamide (DMF) (30 ml) under $N_2$ was added 1-(3-chloropropyl)-1,3-dihydro-2H-benzimidazol-2-one (6.8 g, 0.0232 mol) dissolved in DMF (40 ml). The reaction was stirred at 75° C. for 2.5 hours and then at 85° C. for 18 hours. The reaction was allowed to cool and was then poured into $H_2O$. The aqueous mixture was extracted with ethyl acetate and the ethyl acetate extract was washed with brine, dried with $MgSO_4$ and concentrated to afford 13.0 g of an oil. The oil was purified by HPLC (Water's Prep. LC/System 500A, 2 columns, eluting with 10% methanol-$CH_2Cl_2$) yielding 6.2 g (64%) of a solid. An analytically pure sample was obtained by two recrystallizations of a 6.0 g sample from ethanol-$H_2O$ affording 4.0 g (43%) of 3-{4-[3-(1,3-dihydro-2-oxo-2H-benzimidazol-1-yl)propyl]-1-piperazinyl}-1H-indazole, m.p. 178°–180° C.

| ANALYSIS | | | |
|---|---|---|---|
| Calculated for $C_{21}H_{24}N_6O$ | 66.99% C | 6.44% H | 22.33% N |
| Found | 67.05% C | 6.51% H | 22.27% N |

EXAMPLE 23

4-(1H-indazol-3-yl)-1-piperazinecarboxamide

A solution of 3-(1-piperazinyl)-1H-indazole (5.0 g, 0.0247 mol) of Example 3a, nitrourea (4.2 g, 0.047 mol) and DMF (125 ml) was warmed on a steam bath for 2 hours. The reaction was poured into $H_2O$ and $CH_2Cl_2$ was added. The resultant emulsion was filtered through a bed of celite and the two layers of the filtrate was separated. The $H_2O$ was extracted again with $CH_2Cl_2$ and the organic extracts were combined, washed with $H_2O$, dried with $MgSO_4$ and concentrated to afford 3.7 g of an oil. The celite filter cake was triturated with 30% methanol-$CH_2Cl_2$ and filtrate was concentrated to afford 2.5 g of a solid. The two samples that were obtained were combined (total of 6.2 g) and purified by preparative HPLC (Waters Associates Prep. LC/System 500, 2 silica gel columns, eluting with 10% methanol-$CH_2Cl_2$), yielding 4.0 g of a solid. The sample was taken up in a minimal amount of hot ethyl acetate and filtered. The filtrate was cooled in an ice bath and the resultant crystals were collected and dried to afford 3.2 g (52%) of 4-(1H-indazol-3-yl)-1-piperazinecarboxamide, m.p. 158°–160° C.

| ANALYSIS | | | |
|---|---|---|---|
| Calculated for $C_{12}H_{15}N_5O$ | 58.76% C | 6.16% H | 28.55% N |
| Found | 58.59% C | 6.29% H | 28.38% N |

EXAMPLE 24

3-[4-(2-Hydroxyethyl)-1-piperazinyl]-1H-indazole dihydrochloride

A mixture of 3-(1-piperazinyl)-1H-indazole (5.0 g, 0.0247 mol) of Example 3a, $K_2CO_3$ (3.8 g, 0.0275 mol), 2-bromoethanol (3.4 g, 0.0272 mol) and DMF (100 ml) under $N_2$ was stirred at 50° C. for 7 hours and then at room temperature for 65 hours. The reaction was poured into $H_2O$ and the aqueous mixture extracted with ethyl acetate. The ethyl acetate extract was washed with brine, dried with $MgSO_4$ and concentrated to afford 3.5 g of an oil. The $H_2O$ phase was reextracted with $CH_2Cl_2$ and the organic layer was washed with brine, dried with $MgSO_4$ and concentrated to afford 3.0 g more of an oil. Both samples were combined. The 6.5 g sample was purified by HPLC (Water's Associates Prep. LC/System 500, 2 silica gel columns, eluting with 14% methanol-$CH_2Cl_2$), yielding 4.0 g of an oil. The oil was taken up in anhydrous ether and methanol (minimal amount) and ethereal HCl was added to precipitate 3.7 g of the salt. The compound was recrystallized from methanol-ether to afford 3.4 g (44%) of 3-[4-(2-hydroxyethyl)-1-piperazinyl]-1H-indazole dihydrochloride, m.p. 258°–260° C.

| ANALYSIS | | | |
|---|---|---|---|
| Calculated for $C_{13}H_{18}N_4O.2$ HCl | 48.91% C | 6.31% H | 17.55% N |
| Found | 48.87% C | 6.40% H | 17.56% N |

EXAMPLE 25

3-[4-(Dimethylphosphinylmethyl)-1-piperazinyl]-1H-indazole

A mixture of 3-(1-piperazinyl)-1H-indazole (5.8 g, 0.0287 mol) of Example 3a, $K_2CO_3$ (4.8 g, 0.0344 mol), chloromethyldimethylphosphine oxide (4.4 g, 0.0344 mol) and DMF (100 ml) was stirred at 90° C. under $N_2$ for 26 hours. Most of the DMF was removed in vacuo and the resultant residue was diluted with $H_2O$. The aqueous mixture was extracted with $CH_2Cl_2$. The organic extract was washed with $H_2O$, dried with $MgSO_4$ and concentrated to afford 8.2 g of a solid. The compound was isolated by preparative HPLC (Water's Associates Prep. LC/System 500, 2 silica gel columns, eluting with 7.5% methanol-$CH_2Cl_2$) yielding 4.0 g of a solid. The solid was taken up in a minimal amount of $CH_3CN$, filtered, and the filtrate produced crystals which were collected and dried to afford 3.0 g (36%) of 3-[4-(dimethylphosphinylmethyl)-1-piperazinyl]-1H-indazole, m.p. 223°–225° C.

| ANALYSIS | | | |
|---|---|---|---|
| Calculated for $C_{14}H_{21}N_4OP$ | 57.52% C | 7.24% H | 19.17% N |
| Found | 57.55% C | 7.23% H | 19.24% N |

EXAMPLE 26

3-{4-[3-(2-Methylindol-3-yl)propyl]-1-piperazinyl}-1H-indazole hemifumarate

A mixture of 3-(1-piperazinyl)-1H-indazole (3.0 g, 0.0148 mol) of Example 3a, $K_2CO_3$ (2.1 g, 0.0148 mol), 3-(3-phenylsulfonyloxypropyl)-2-methylindole (4.9 g, 0.0148 mol) and DMF (75 ml) was stirred at 75° C. for 3.5 hours. The reaction mixture was poured into $H_2O$ and extracted with ethyl acetate. The ethyl acetate extract was washed with brine, dried with $MgSO_4$ and concentrated to afford 5.6 g of an oil. The oil was purified by two consecutive runs on preparative HPLC (Water's Associates Prep. LC/System 500A, 2 silica gel columns per run), eluting first with 6% methanol-$CH_2Cl_2$, to afford 5.0 g of an oil. Subsequent chromatography was affected utilizing 5% diethylamine-ethyl acetate as eluent, and concentration of the appropriate fractions yielded 4.2 g (76%) of a gum. A hemifumarate was prepared by dissolving the sample in ethyl acetate (100 ml) and adding fumaric acid (2.0 g, 1.5 eq). The mixture was heated on a steam bath at reflux for 5 minutes and then stirred at ambient temperature for 5 hours. The resulting salt was collected by filtration yielding 4.9 g of a solid. The compound was triturated with hot methanol and filtered while still hot affording 2.0 g. The sample was combined with an additional sample (total of 3.8 g), and the salt was reprecipitated by dissolving the compound in DMF (minimal amount) and adding hot $H_2O$ while scratching. The solid which formed was collected and washed well with $H_2O$ and then dried in a vacuum oven at 100° C. for 3 hours. A total of 2.2 g (17%) of 3-{4-[3-(2-methylindol-3-yl)propyl]-1-piperazinyl}-1H-indazole hemifumarate, m.p. 226°–228° C.

| ANALYSIS | | | |
|---|---|---|---|
| Calculated for $C_{23}H_{27}N_5.0.5C_4H_4O_4$ | 69.57% C | 6.79% H | 16.23% N |
| Found | 68.78% C | 6.69% H | 15.90% N |

EXAMPLE 27

3-(4-Ethyl-1-piperazinyl)-1H-indazole

To a stirred mixture of 3-(1-piperazinyl)-1H-indazole (5.0 g, 0.0247 mol) of Example 3a, $K_2CO_3$ (3.8 g, 0.0275 mol) dimethylformamide (DMF) [75 ml] was added, dropwise, bromoethane (3.0 g, 0.0275 mol) in DMF (10 ml). The reaction was stirred at 58° C. for 2.25 hours and was then poured into $H_2O$. The aqueous mixture was extracted with ethyl acetate. The ethyl acetate extract was washed twice with brine, dried with $MgSO_4$ and the solvent was removed in vacuo to yield 6.0 g of a liquid which produced a solid upon scratching. The product was purified by preparative HPLC (Water's Associates Prep. LC/System 500, 2 silica gel columns, eluting with 5% diethylamine-ethyl acetate). Concentration of appropriate fractions afforded 3.5 g of a solid. The compound was taken up in anhydrous ether and ethereal HCl was added to precipitate 4.4 g of the salt. Two recrystallizations from methanol-ether afforded 3.1 g of 3-(4-ethyl-1-piperazinyl)-1H-indazole, m.p. 306°–308° C.

| ANALYSIS | | | |
|---|---|---|---|
| Calculated for $C_{13}H_{18}N_4.2HCl$ | 51.49% C | 6.65% H | 18.48% N |
| Found | 51.85% C | 6.76% H | 18.56% N |

EXAMPLE 28

3-[4-(2-Phenylethyl)-1-piperazinyl]-1H-indazole

A mixture of 3-(1-piperazinyl)-1H-indazole (5.0 g, 0.0247 mol) of Example 3a, $K_2CO_3$ (3.4 g, 0.0247 mol), (2-bromoethyl)benzene (5.1 g, 0.0272 mol) and DMF (75 ml) was stirred at 75° C. for 3 hours and then at ambient temperatures for 1 hour. The mixture was poured into $H_2O$ and then extracted with ethyl acetate. The ethyl acetate extract was washed with brine, dried with $MgSO_4$ and the solvent was concentrated to afford 8.0 g of an oil. The compound was purified by preparative HPLC (Water's Associates Prep. LC System 500A; 2 silica gel columns, eluting with 3% diethylamine-ethyl acetate) yielding 4.5 g (59%) of a solid which appeared pure by TLC. Recrystallization from toluene afforded 3.5 g of 3-[4-(2-phenylethyl)-1-piperazinyl]-1H-indazole, m.p. 118°–120° C.

| ANALYSIS | | | |
| --- | --- | --- | --- |
| Calculated for $C_{19}H_{22}N_4$ | 74.48% C | 7.24% H | 18.28% N |
| Found | 74.56% C | 7.23% H | 18.21% N |

EXAMPLE 29

3-{4-[3-(6-Fluoro-1,2-benzisoxazol-3-yl)propyl]-1-piperazinyl}-1H-indazole

A mixture of 3-(1-piperazinyl)-1H-indazole (5.0 g, 0.0237 mol) of Example 3a, $K_2CO_3$ (3.8, 0.0247 mol), 3-(3-chloropropyl)-6-fluoro-1,2-benzisoxazole (5.8 g, 0.0272 mol) and DMF (75 ml) was stirred at 150° C. for 4 hours. The reaction was poured into $H_2O$ and the aqueous mixture extracted with ethyl acetate. The extract was washed ($H_2O$), dried ($MgSO_4$) and the solvent concentrated to afford 8.8 g of an oil. A 7.7 g sample of the oil was purified by preparative HPLC (Water's Associates Prep. LC System 500A, 2 silica gel columns, eluting with 7% methanol) yielding 3.5 g (42%) of a solid. Recrystallization from ethanol afforded 2.3 g of 3-{4-[3-(6-fluoro-1,2-benzisoxazol-3-yl)propyl]-1-piperazinyl}-1H-indazole, m.p. 139°–141° C.

| ANALYSIS | | | |
| --- | --- | --- | --- |
| Calculated for $C_{21}H_{22}FN_5O$ | 66.48% C | 5.84% H | 18.46% N |
| Found | 66.16% C | 5.59% H | 18.39% N |

EXAMPLE 30

3-[4-[4,4-Bis(4-fluorophenyl)butyl-1-piperazinyl]-1H-indazole hydrochloride

A mixture of 3-(1-piperazinyl)-1H-indazole (2.7 g, 0.013 mol) of Example 3a, $K_2CO_3$ (1.8 g), 1,1-bis(4-fluorophenyl)-4-methylsulfonyloxybutane (4.5 g, 0.013 mol) and DMF (75 ml) was stirred and heated at 75° C. for 5 hours. The reaction was poured into $H_2O$ and the aqueous mixture was extracted with ethyl acetate. The extract was washed ($H_2O$), dried ($MgSO_4$) and concentrated to afford 5.4 g of an oil. The oil was chromatographed on a Water's Associates Prep. 500 HPLC, on silica gel columns, with $CH_2Cl_2$-methanol (3%) as eluent. Concentration of the appropriate fractions afforded a foam, which when triturated with refluxing hexane yielded 2.1 g of a solid. The solid was dissolved in absolute ethanol (50 ml) and ethereal HCl was added until the solution was acidic. The resultant, insoluble, hydrochloride salt was collected and dried to afford 2.4 g (38%) of 3-[4-[4,4-bis(4-fluorophenyl)butyl-1-piperazinyl]-1H-indazole hydrochloride, m.p. 238°–240° C.

| ANALYSIS | | | |
| --- | --- | --- | --- |
| Calculated for $C_{27}H_{28}F_2N_4 \cdot HCl$ | 67.41% C | 6.05% H | 11.60% N |
| Found | 66.72% C | 6.14% H | 11.60% N |

EXAMPLE 31 a. 2-Chloro-4-fluorobenzoic acid 2-phenylsulfonylhydrazide

To a stirred mixture under $N_2$ of 2-chloro-4-fluorobenzoic acid hydrazide (58.4 g, 0.289 mol) in dry pyridine (250 ml), was added, dropwise, at 5° C., benzenesulfonyl chloride (52.0 g, 37 ml, 0.289 mol). After complete addition the reaction was stirred at ambient temperature for 16 hours. The reaction was poured into ice 6N-HCl (about 450 ml) and the product separated as an oil. The aqueous mixture was extracted with ethyl acetate. The ethyl acetate was washed ($H_2O$), dried ($MgSO_4$) and concentrated to afford 85.2 g of a solid, m.p. 135°–137° C. This was recrystallized from ethanol-water to afford 74.1 g of 2-chloro-4-fluorobenzoic acid 2-phenylsulfonylhydrazide, m.p. 147°–149° C.

b. α-Chloro-2-chloro-4-fluorobenzaldehyde phenylsulfonylhydrazone

A mixture of 2-chloro-4-fluorobenzoic acid 2-phenylsulfonylhydrazide (314 g, 0.96 mol) of Example 31a and $SOCl_2$ (450 ml) was stirred and refluxed for 2 hours. Most of the $SOCl_2$ was distilled, resulting in a solid. The solid was triturated with hexane and the solid was collected by filtration and immediately recrystallized from toluene-hexane to afford 281.4 g, (84%) of a solid, m.p. 132°–134° C. An analytical sample was obtained by a subsequent recrystallization (4.0 g sample) from toluene to afford 2.5 g of α-chloro-2-chloro-4-fluorobenzaldehyde phenylsulfonylhydrazone, m.p. 133°–135° C.

| ANALYSIS | | | |
| --- | --- | --- | --- |
| Calculated for $C_{13}H_9Cl_2FN_2O_2S$ | 44.97% C | 2.61% H | 8.07% N |
| Found | 45.51% C | 2.53% H | 8.14% N | c. 6-Fluoro-1-phenylsulfonyl-3-(4-methyl-1-piperazinyl)-1H-indazole

To a stirred solution of α-chloro-4-fluorobenzaldehyde phenylsulfonylhydrazone (58.2 g, 0.017 mol) of Example 31b in THF (300 ml) was added, dropwise, 1-methylpiperazine (35.3 g, 0.35 mol). The reaction was exothermic, causing the temperature to rise to 47° C. After complete addition of the piperazine, the reaction was stirred at ambient temperature for 2 hours. It was then cooled in an ice bath until the temperature was about 10° C. and the insolubles were filtered off. The filtrate was concentrated to afford an oil, which upon trituration with $CH_3CN$ afforded an unwanted solid which was filtered off. The $CH_3CN$ filtrate was concentrated to a solid which was triturated with hexane and filtered to yield 36.5 g of 1-{[(phenylsulfonyl)hydrazone](2-chloro-4-fluorophenyl)methyl}-4-methylpiperazine. The crude hydrazonopiperazine isolated above (25.5 g, 0.086 mol), $K_2CO_3$ (14.3 g, of 0.10 mol), copper-bronze (2.0 g) and DMF (300 ml) was stirred and refluxed for 2 hours. After cooling, the reaction was poured into H2O and ethyl acetate, followed by vigorous stirring of the biphasic mixture. The mixture was filtered through celite and the organic layer was separated. The aqueous phase was extracted twice more with ethyl acetate, and then the combined organic extract was washed (H2O), dried (MgSO4) and concentrated to afford a dark, brown solid. The solid was triturated with ether and was filtered to afford 16.0 g of the product. Recrystallization from isopropanol (charcoal treatment) afforded 12.9 g (39%) of a solid. An analytical sample was obtained by a subsequent recrystallization of a 4.0 g sample from isopropanol (charcoal treatment) to yield 2.8 g of 6-fluoro-1-phenylsulfonyl-3-(4-methyl-1-piperazinyl)-1H-indazole, m.p. 159°–161° C.

| ANALYSIS | | | |
|---|---|---|---|
| Calculated for $C_{18}H_{19}FN_4O_2S$ | 57.74% C | 5.11% H | 14.96% N |
| Found | 57.60% C | 5.11% H | 15.04% N | d. 6-Fluoro-3-(4-methyl-1-piperazinyl)-1H-indazole

To a stirred solution of N2, of 6-fluoro-1-phenylsulfonyl-3-(4-methyl-1-piperazinyl)-1H-indazole (5.0 g, 0.013 mol) of Example 31c in THF (70 ml) was added dropwise, lithium aluminum hydride (20 ml of a 1M solution in THF). The reaction was then stirred and refluxed for 6 hours and then was stirred at ambient temperature for 14 hours. The reaction was cooled in an ice bath, water was added cautiously and the reaction mixture was filtered. The filtrate was concentrated to yield a wet solid. Aqueous saturated sodium carbonate was added to the solid, and the aqueous suspension was extracted with CH2Cl2. The CH2Cl2 extract was washed (brine), dried (K2CO3) and concentrated to afford 2.4 g of a solid. Combining this material with another batch (1.9 g), and recrystallization twice from toluene afforded 2.8 g (53%) of 6-fluoro-3-(4-methyl-1-piperazinyl)-1H-indazole, m.p. 164°–166° C.

| ANALYSIS | | | |
|---|---|---|---|
| Calculated for $C_{12}H_{15}FN_4$ | 61.52% C | 6.45% H | 23.91% N |
| Found | 61.60% C | 6.42% H | 23.88% N |

EXAMPLE 32

1-Benzoyl-6-fluoro-3-(4-methyl-1-piperazinyl)-1H-indazole

A mixture of 6-fluoro-3-(4-methyl-1-piperazinyl)-1H-indazole (3.7 g, 0.016 mol) of Example 31d and benzoyl chloride (10 ml) were heated on a steam bath for 2 hours. After cooling, ether was added to the residue, and 5.6 g of a solid was collected. The solid was suspended in H2O and the mixture was made basic with NH4OH. The aqueous suspension was then extracted with CH2Cl2. The organic extract was washed (H2O), dried (MgSO4) and concentrated to afford a solid which was triturated with hexane and collected, affording 4.2 g of the benzoylated indazole. The compound was recrystallized from ethyl acetate and then from isopropyl ether to afford 2.2 g (42%) of 1-benzoyl-6-fluoro-3-(4-methyl-1-piperazinyl)-1H-indazole, m.p. 146°–148° C.

| ANALYSIS | | | |
|---|---|---|---|
| Calculated for $C_{19}H_{19}FN_4O$ | 67.44% C | 5.66% H | 16.56% N |
| Found | 67.15% C | 5.63% H | 16.55% N |

EXAMPLE 33 a. 4-(6-Fluoro-1-phenylsulfonyl-1H-indazol-3-yl)-1-piperazinecarbonitrile

To a stirred mixture, under N2 of 6-fluoro-1-phenylsulfonyl-3-(4-methyl-1-piperazinyl)-1H-indazole (30.0 g, 0.86 mol) of Example 31c, K2CO3 (4.7 g, 0.086 mol) and dimethyl sulfoxide (DMSO) [250 ml] was added, dropwise, BrCN (9.1 g, 0.086 mol) dissolved in DMSO (50 ml). The reaction was stirred at ambient temperature for 2 hours and water was added. The resultant solid was collected and taken up in CH2Cl2, and after washing the organic layer with H2O, drying (K2CO3) and concentrating there remained 25.3 g of the target compound. A sample (5.0 g) was removed and recrystallized from ethyl acetate (twice) to afford 2.3 g (35%) of 4-(6-fluoro-1-phenylsulfonyl-1H-indazol-3-yl)-1-piperazine carbonitrile m.p. 178°–180° C.

| ANALYSIS | | | |
|---|---|---|---|
| Calculated for $C_{18}H_{16}FN_5O_2S$ | 56.10% C | 4.18% H | 18.18% N |
| Found | 36.05% C | 3.73% H | 18.15% N | b. 6-Fluoro-3-(1-piperazinyl)-1H-indazole Hydrochloride

To a stirred mixture under N2 of 4-(6-fluoro-1-phenylsulfonyl-1H-indazol-3-yl)-1-piperazinecarbonitrile (25.4 g, 0.068 mol) of Example 33a in tetrahydrofuran (THF) [400 ml], was added, dropwise, lithium aluminum hydride in THF (130 ml of a 1M solution). The reaction was stirred and refluxed for 3 hours, cooled in an ice bath and H2O was added, dropwise. The reaction was filtered and the filter cake was washed well with THF and then twice with methanol. Concentration of the filtrate afforded a gum, which when triturated with ether afforded 14.6 g of a solid. The solid was dissolved in methanol (warming) and ethereal HCl was added to the solution until it was acidic. Ether was then added to the solution, which initially precipitated a gum. The supernatant solution was decanted from the gum, and upon addition of more ether to the solution 5.4 g of a hydrochloride salt was collected. Trituration of the gum with refluxing ethyl acetate gave an additional 3.2 g of salt (crude yield, 49%). The latter salt was recrystallized from methanol-ether (twice) to afford 2.2 g of 6-fluoro-3-(1-piperazinyl)-1H-indazole hydrochloride, m.p. 268°–270° C.

| ANALYSIS | | | |
|---|---|---|---|
| Calculated for $C_{11}H_{13}FN_4 \cdot HCl$ | 51.48% C | 5.50% H | 21.83% N |
| Found | 51.38% C | 5.37% H | 21.61% N |

EXAMPLE 34

6-Fluoro-3-{4-[3-(1,3-dihydro-2-oxo-2H-benzimidazol-1-yl)propyl]-1-piperazinyl}-1H-indazole Hemifumarate A mixture of 6-fluoro-3-(1-piperazinyl)-1H-indazole hydrochloride 5.0 g, 0.02 mol) of Example 33b, NaHCO$_3$ (3.7 g, 0.044 mol), 1-(3-chloropropyl)-1,3-dihydro-2H-benzimidazol-2-one (4.6 g, 0.022 mol) and dimethylformamide (DMF) (60 ml) was stirred and heated at 90° C. for 16 hours. The mixture was poured into H$_2$O and the aqueous mixture extracted with ethyl acetate. The extract was washed (H$_2$O), dried (MgSO$_4$) and was concentrated to afford 7.7 g of a gum. The gum was chromatographed on a Water's Associated Prep. LC/System 500 (silica gel 8% methanol/CH$_2$Cl$_2$ as eluent) to yield 4.1 g of a foam. A fumarate salt was prepared by dissolving the foam in acetone, adding fumaric acid (1.3 g, 1.1 equiv.), and warming on a steam bath for at least 3 minutes. The fumarate salt precipitated from solution and was collected to afford 4.1 g of a solid. Recrystallization from methanol-ether yielded 2.8 g (31%) of 6-fluoro-3-{4-[3-(1,3-dihydro-2-oxo-2H-benzimidazol-1-yl)propyl]-1-piperazinyl}-1H-indazole hemifumarate, m.p. 236°–238° C.

| ANALYSIS | | | |
|---|---|---|---|
| Calculated for C$_{21}$H$_{23}$FN$_6$O.0.5C$_4$H$_4$O$_4$ | 61.04% C | 5.57% H | 18.56% N |
| Found | 60.89% C | 5.66% H | 18.5% N |

EXAMPLE 35

3-{4-[4,4-Bis(4-fluorophenyl)butyl]-1-piperazinyl}-6-fluoro-1H-indazole hydrochloride A mixture of 6-fluoro-3-(1-piperazinyl)-1H-indazole (2.8 g, 0.013 mol) Example 33b, K$_2$CO$_3$ (1.7 g) and 1,1-bis(4-fluorophenyl)-4-methylsulfonyloxybutane (4.5 g, 0.013 mol) and DMF (75 ml) was stirred and heated at 75° C. for 6 hours. The reaction mixture was poured into H$_2$O, and the aqueous mixture extracted with ethyl acetate to afford 6.9 g of an oil. The oil was flash chromatographed on silica gel (ethyl acetate- 8% diethylamine as eluent) to afford 3.3 g of an oil, which partially solidified. This was combined with another sample (1.2 g) and a fumarate salt was prepared. Suitable purity of the salt could not be achieved, therefore the salt was reversed to the free base and subjected to preparative HPLC (silica gel; CH$_2$Cl$_2$/methanol, 10%). Concentration of the appropriate fractions yielded 3.0 g of an oil, which was converted to 3.0 g of a hydrochloride salt with ethereal HCl. Recrystallization from ethanol afforded 0.9 g of a solid which melted at 189°–191° C. Concentration of the mother liquors followed by addition of ether gave 1.3 g of a solid, m.p. 192°–195° C. It was determined that the initial material which formed had occluded ethanol, and drying this sample at 110° C. and a pressure of 1 mm yielded 0.8 g of the salt with a melting point identical to the second crop of crystals. The total yield was thus 2.1 g (25%) of 3-{4-[4,4-bis(4-fluorophenyl)butyl]-1-piperazinyl}-6-fluoro-1H-indazole hydrochloride.

| ANALYSIS | | | |
|---|---|---|---|
| Calculated for C$_{27}$H$_{27}$F$_3$N$_4$.HCl | 64.73% C | 5.43% H | 11.18% N |
| Found | 64.67% C | 5.52% H | 11.12% N |

EXAMPLE 36 a. 4-(5-Chloro-1H-indazol-3-yl)-1-piperazinecarbonitrile

To a stirred mixture of 5-chloro-3-(4-methyl-1-piperazinyl)-1H-indazole (7.0 g, 0.028 mol), K$_2$CO$_3$ (4.3 g, 0.0314 mol) and dimethyl sulfoxide (DMSO) [100 ml] under N$_2$ was added, dropwise, BrCN (3.0 g, 0.028 mol) dissolved in DMSO (40 ml). The reaction was stirred at ambient temperature for 3 hours and was then poured into H$_2$O (250 ml). A precipitate formed overnight and was collected and washed with H$_2$O and dried to afford 4.0 g of a solid. The aqueous layer was concentrated down to a liquid which was diluted with H$_2$O (150 ml) and extracted with ethyl acetate. The ethyl acetate was washed with H$_2$O, dried (MgSO$_4$) and concentrated to afford a liquid. The liquid was taken up in ether-methanol and ethereal HCl was added to precipitate 1.4 g of a solid. The solid was converted back to the free base which yielded 800 mg of of a solid of 4-(5-chloro-1H-indazol-3-yl)-1-pierazinecarbonitrile.

b. 5-Chloro-3-(1-piperazinyl)-1H-indazole

To a stirred solution of 4-(5-chloro-1H-indazol-3-yl)-1-piperazinecarbonitrile of Example 36a in THF (175 ml) under N$_2$ was added, dropwise, lithium aluminum hydride (20 ml, 0.02 mol of a 1M lithium aluminum hydride solution in THF). After total addition, the reaction was heated to reflux and stirred for 3 hours. The reaction was cooled in an ice bath and the excess lithium aluminum hydride was destroyed by the dropwise addition of H$_2$O (15 ml). This was filtered through a coarse sintered glass funnel and the filter cake was washed well with THF. The filtrate was concentrated to afford a biphasic H$_2$O-oil (7.5 g). This was partitioned between CH$_2$Cl$_2$ and H$_2$O and the H$_2$O was extracted again with CH$_2$Cl$_2$ adding a small amount of saturated NaCl solution. The combined CH$_2$Cl$_2$ extract was washed with H$_2$O, dried with MgSO$_4$ and concentrated to afford 3.2 g of a solid, m.p. 60°–62° C. The solid was purified by preparative HPLC (Water's Associates Prep. LC/System 500, 2 silica gel columns eluting with 20% methanol-CH$_2$Cl$_2$) to afford 1.9 g of product. A small amount was recrystallized from toluene and collected, then washed with hexane affording solid 5-chloro-3-(1-piperazinyl)-1H-indazole, m.p. 178°–180° C.

| ANALYSIS | | | |
|---|---|---|---|
| Calculated for C$_{11}$H$_{13}$N$_4$Cl | 55.81% | 5.55% H | 23.64% N |
| Found | 55.28% C | 5.41% H | 22.83% N |

EXAMPLE 37

3-{4-[4,4-bis(4-fluorophenyl)butyl-1-piperazinyl}-5-chloro-1H-indazole hydrochloride A mixture of 5-chloro-3-(1-piperazinyl)-1H-indazole (1.9 g, 0.008 mol) of Example 36c potassium carbonate (1.2 g, 0.008 mol), 1,1-bis(4-fluorophenyl)-4-methylsulfonyloxybutane (2.7 g, 0.008 mol) and dimethylformamide (DMF) [75 ml] under N$_2$ was stirred at 75° C. for 4.5 hours. The cooled reaction was poured into H$_2$O and the aqueous mixture was extracted with ethyl acetate. The ethyl acetate extract was washed with H$_2$O, dried with MgSO$_4$ and concentrated to afford 4.3 g of an oil. The sample was purified by preparative HPLC (Water's Associates Prep/LC System 500 utilizing 2 silica gel columns and 2% diethylamine-ethyl acetate as eluent) to yield 2.2 g of a gum. The gum was dissolved in absolute ethanol (60 ml) and ethereal HCl was added until the solution was acidic. A solid began precipitating from the stirred solution within 5 minutes following addition. The mixture was collected and dried to afford 2.0 g (49%) of the hydrochloride salt. The solid was recrystallized from ethanol-ether to afford 1.7 g (41%) of 3-{4-[4,4-bis(4-fluorophenyl)butyl-1-piperazinyl}-5-chloro-1H-indazole hydrochloride, m.p. 225°–227° C.

| ANALYSIS | | | |
|---|---|---|---|
| Calculated for C$_{27}$H$_{28}$ClF$_2$N$_4$.HCl | 62.66% C | 5.46% H | 10.83% N |
| Found | 62.82% C | 5.43% H | 10.71% N |

EXAMPLE 38 a. 2,4-Dichlorobenzoic acid hydrazide

To a stirred solution under N$_2$ of ethyl 2,4-dichlorobenzoate (517 g, 236 mol) in absolute ethanol (1.6 l) was added, dropwise, hydrazine monohydrate (675 ml, 697 g, 13.9 mol) over the course of one hour. About 10 minutes after complete addition product began falling out of solution, nevertheless, the reaction mixture was stirred for an additional 1.5 hours, and then stood overnight. The mixture was cooled 0° C.–10° C. in ice-salt bath and then filtered. The resultant solid was washed with cold ethanol and the solid was dried and weighed to provide 438.5 g (91%) of the desired hydrazide. The filtrate was concentrated to yield a wet solid which was diluted out with H$_2$O, filtered, dried and weighed to provide 36.5 g of 2,4-dichlorobenzoic acid hydrazide. This gave a total of yield of 475 g (98%).

b. 2,4-Dichlorobenzoic acid 2-phenylsulfonyl hydrazide

To a stirred mixture of 2,4-dichlorobenzoic acid hydrazide (470.0 g, 2.29 mol) of Example 38a in dry pyridine (3.31), under N$_2$ and cooled to 0° in an ice-salt bath, was added dropwise, benzenesulfonyl chloride 396.0 g, (2.29 mol) so that the reaction did not exceed 12° C. After complete addition, the reaction was stirred for 4 hours at ambient temperature. Most of the pyridine was removed in vacuo and the resultant thick liquid was poured into ice-HCl. The solid which formed was collected by filtration and was washed well with H$_2$O and dried to yield a solid. The solid was recrystallized from isopropyl alcohol to afford 699.0 g (88%) of a white solid. A 5.0 g sample was recrystallized twice from isopropyl alcohol to give 3.1 g of 2,4-dichlorobenzoic acid 2-phenylsulfonyl hydrazide, mp 168°–170° C.

| ANALYSIS | | | |
|---|---|---|---|
| Calculated for C$_{13}$H$_{10}$Cl$_2$N$_2$O$_3$S | 45.23% C | 2.92% H | 8.11% N |
| Found | 45.18% C | 2.81% H | 8.11% N | c. α-Chloro-2,4-dichlorobenzaldehyde-2-phenylsulfonylhydrazone

A mixture of 2,4-dichlorobenzoic acid 2-phenylsulfonyl hydrazide (600.0 g, 1.74 mol), and thionyl chloride (21) was stirred at reflux for 21 hours and was allowed to stand for 65 hours. About half of the thionyl chloride was distilled off from the reaction and the cooled mixture was poured into hexane. The solid was collected by filtration and was washed well with hexane yielding 480.0 g (76%). The batch was recrystallized from toluene to afford 430.0 g (60%). A 5.0 g sample was recrystallized twice from toluene (utilizing decolorizing carbon) to provide 2.9 g (40%) of α-chloro-2,4-dichlorobenzaldehyde-2-phenylsulfonylhydrazone, mp 135°–137° C.

| ANALYSIS | | | |
|---|---|---|---|
| Calculated for C$_{13}$H$_9$Cl$_3$N$_2$O$_2$S | 42.94% C | 2.49% H | 7.70% N |
| Found | 43.19% C | 2.44% H | 7.63% N | d. 1-{[(Phenylsulfonyl)hydrazono](2,4-dichlorophenyl)methyl}-4-methylpiperazine To a stirred solution of α-chloro-2,4-dichlorobenzaldehyde-2-phenyl sulfonylhydrazone (425.0 g, 1.17 mol) of Example 38c in tetrahydrofuran (THF) (2.3 l), under N$_2$ and cooled to 4° C. in an ice-salt bath, was added, dropwise, 1-methylpiperazine (258.0 g, 2.57 mol). After complete addition, the bath was removed and the reaction was stirred at ambient temperature for 5 hours and was then allowed to stand overnight (about 16 hours). The reaction mixture was cooled again in an ice bath and filtered. The filter cake was washed well with cold THF and the filtrate was concentrated to yield 186.0 g of an oil. The oil was triturated with CH$_3$CN and filtered. The filter cake was washed with CH$_3$CN and the filtrate concentrated to afford 120.0 g (25%) of a solid. A 5.0 g sample was recrystallized twice from isopropyl alcohol to provide 3.2 g of 1-{[(phenylsulfonyl)hydrazono](2,4-dichlorophenyl)methyl}-4-methylpiperazine, mp 174°–176° C.

| ANALYSIS: | | | |
|---|---|---|---|
| Calculated for C$_{18}$H$_{20}$C$_{12}$N$_4$O$_2$S: | 50.59% C | 4.72% H | 13.11% N |
| Found: | 60.56% C | 4.71% H | 13.09% N | e. 3-(4-Methyl-1-piperazinyl)-6-chloro-1-phenylsulfonyl-1H-indazole

A mixture of 1-{[(phenylsulfonyl)hydrazono](2,4-dichlorophenyl)methyl}-4-methylpiperazine (10.0 g, 0.0234 mol) of Example 38d, potassium carbonate (3.9 g, 0.0281 mol), copper-bronze (700 mg) and dimethylformamide (100 ml) was stirred at reflux for 6 hours under N$_2$. The cooled reaction was poured into H$_2$O and ethyl acetate was added. The bisphasic mixture was stirred vigorously for 10 minutes and was then filtered through celite. The filter cake was washed well with ethyl acetate and the two phases of the filtrate were separated. The H$_2$O layer was extracted further with ethyl acetate and the combined ethyl acetate extract was washed with H$_2$O, dried with MgSO$_4$ and concentrated to yield 6.5 g of an oily residue. The sample was purified by preparative HPLC (Water's Associates Prep. LC/System 500A, utilizing 2 silica gel columns and 5% methanol-CH$_2$Cl$_2$ as eluent) to afford 4.4 g (48%) of a solid. The material was recrystallized from isopropyl alcohol to yield 3.7 g and a subsequent recrystallization from isopropyl alcohol and treatment with decolorizing carbon provided 3.2 g (35%) of 3-(4-methyl-1-piperazinyl)-6-chloro-1-phenylsulfonyl-1H-indazole, mp 139°–141° C.

ANALYSIS:

| | | | |
|---|---|---|---|
| Calculated for C$_{18}$H$_{19}$ClN$_4$O$_2$S: | 55.31% C | 4.90% H | 14.35% N |
| Found: | 55.38% C | 4.86% H | 14.34% N |

EXAMPLE 39 a. 4-(6-Chloro-1-phenylsulfonyl-1H-indazol-3-yl)-1-piperazinecarbonitrile

To a stirred mixture of 3-(4-methyl-1-piperazinyl)-6-chloro-1-phenylsulfonyl-H-indazole of Example 38a (352.0 g, 0.90 mol), potassium carbonate (136.9 g, 0.99 mol) and dimethyl sulfoxide (2.3 l) was added, dropwise, cyanogen bromide (96.4 g, 0.910 mol) dissolved in (700 ml). After complete addition, the reaction was stirred at room temperature under N$_2$ for 1 hour. The mixture was partitioned between H$_2$O and ethyl acetate and concentration of the organic phase afforded a wet solid. Residual H$_2$O was removed from the material by azeotropic distillation with toluene. The resultant damp solid was triturated with warm toluene and the product was isolated by filtration to yield 198.0 g of a solid. A 5.0 g sample was recrystallized from isopropyl alcohol to afford 4.0 g. Subsequent recrystallization from isopropyl alcohol (with decolorizing carbon) provided 3.4 g (37%) 4-(6-chloro-1-phenylsulfonyl-1H-indazol-3-yl)-1-piperazinecarbonitrile, mp 179°–181° C.

ANALYSIS:

| | | | |
|---|---|---|---|
| Calculated for C$_{18}$H$_{16}$ClN$_5$O$_2$S: | 53.80% C | 4.01% H | 17.43% N |
| Found: | 53.73% C | 3.94% H | 17.35% N | b. 6-Chloro-3-(1-piperazinyl)-1H-indazole

To a stirred suspension of 4-(6-chloro-1-phenylsulfonyl-1H-indazol-3-yl)-1-piperazinecarbonitrile (192.5 g, 0.497 mol) of Example 39a in dry tetrahydrofuran (THF) (3.5 l) under N$_2$ was added, dropwise, LiAlH$_4$ (958 ml of a 1.0M solution of LiAlH$_4$ in THF; 0.958 mol). After complete addition the reaction was heated to reflux and stirred under N$_2$ for 4 hours. The reaction was cooled to 4° C. in an ice-salt bath and the excess LiAlH$_4$ was destroyed by the careful dropwise addition of H$_2$O. The mixture was stirred vigorously for an additional 30 minutes and was then filtered through a coarse sintered glass funnel. The filter cake was washed well three times with 500 ml portions of (THF) and then twice with methanol and the filtrate was concentrated to yield 151.0 g of a gum. Trituration with ether afforded a solid, which was collected and dried to give 75.0 g (66%) of the desired indazole. A 4.0 g sample was recrystallized from toluene to yield 3.2 g, which was recrystallized again from toluene (utilizing decolorizing carbon) to provide 2.1 g (35%) of 6-chloro-3-(1-piperazinyl)-1H-indazole, mp 135°–137° C.

ANALYSIS:

| | | | |
|---|---|---|---|
| Calculated for C$_{11}$H$_{13}$ClN$_6$: | 55.82% C | 5.54% H | 23.67% N |
| Found: | 55.91% C | 5.54% H | 23.41% N |

EXAMPLE 40

3-{4-[4,4-Bis(4-fluorophenyl)butyl]-1-piperazinyl}-6-chloro-1H-indazole hemifumarate A mixture of 6-chloro-[3-(1-piperazinyl)]-1H-indazole (2.5 g, 0.0106 mol) of Example 39g, 1,1-bis(4(4-fluorophenyl)-4-methylsulfonyloxybutane (4.0 g, 0.0116 mol), potassium carbonate (1.9 g, 0.0137 mol) and CH$_3$CN (100 ml) was stirred at reflux under N$_2$ for 4.5 hours. The reaction was filtered and the filter cake was washed well with CH$_3$CN. The filtrate was concentrated to an oily residue, which was partitioned between H$_2$O and ethyl acetate. The ethyl acetate extract was washed with H$_2$O, dried with MgSO$_4$ and concentrated to yield 6.0 g of an oil. The oil was purified by preparative HPLC (Water's Associates Prep. LC/System 500A utilizing 2 silica gel columns and 4% methanol-CH$_2$Cl$_2$ as eluant) to provide 3.3 g of a solid. The compound was taken up in ethyl acetate (90 ml) and fumaric acid (0.81 g) was added. The mixture was stirred at a mild reflux for 45 minutes and then at ambient temperature for 1.5 hours. The resultant solid was collected and dried to yield 3.4 g. This was combined with another sample (5.0 g total) and two consecutive recrystallizations from absolute ethanol provided 3.0 g (22%) of 3-{4-[4,4-bis(4-fluorophenyl)butyl]-1-piperazinyl}-6-chloro-1H-indazole hemifumarate, mp 202°–204° C.

ANALYSIS:

| | | | |
|---|---|---|---|
| Calculated for C$_{27}$H$_{27}$ClF$_2$N$_4$.0.5C$_4$H$_4$O$_4$: | 64.61% C | 5.43% H | 10.40% N |
| Found: | 64.59% C | 5.43% H | 10.39% N |

EXAMPLE 41

1-Benzoyl-3-{4-[4,4-bis(4-fluorophenyl)butyl]-1-piperazinyl}-6-chloro-1H-indazole hydrochloride A mixture of 3-{4-[4,4-bis(4-fluorophenyl)butyl]-1-piperazinyl-6-chloro-1H-indazole (2.6 g, 0.0054 mol) of Example 40 and benzoyl chloride (18.2 g, 0.1295 mol) was heated on a steam bath under N$_2$ for 1.25 hours. The mixture was cooled to room temperature and diluted with anhydrous ether (200 ml). The product was filtered and washed well with ether, and dried to yield 2.8 g of a solid. Two recrystallizations from absolute ethanol provided 1.8 g (53%) of 1-benzoyl-3-{4-[4,4-bis(4-fluorophenyl)butyl]-1-piperazinyl}-6-chloro-1H-indazole hydrochloride, mp 228°–230° C.

ANALYSIS:

| | | | |
|---|---|---|---|
| Calculated for C$_{34}$H$_{31}$ClF$_2$N$_4$O.HCl: | 65.70% C | 5.19% H | 9.01% N |
| Found: | 66.16% C | 5.16% H | 9.03% N |

EXAMPLE 42

3-{4-[4,4-bis(4-fluorophenyl)butyl]-1-piperazinyl}-5-methoxy-1H-indazole fumarate A mixture of 5-methoxy-3-(1-piperazinyl)-1H-indazole (2.0 g, 0.0086 mol), potassium carbonate (1.5 g, 0.00109 mol), 1,1-bis(4-fluorophenyl)-4-methanesulfonylbutane (2.9 g, 0.0086 mol) and dimethylformamide (DMF) [50 ml] was stirred at 65° C. under $N_2$ for 18 hours. The cooled reaction was poured into $H_2O$ and the aqueous mixture was extracted with ethyl acetate. The organic extract was washed with brine, dried with $MgSO_4$ and concentrated to afford 5.0 g of an oil. The oil was purified by preparative HPLC (Water's Associates Prep. LC/System 500A, 2 silica gel columns, eluting with 3% methanol-$CH_2Cl_2$) to yield 1.8 g (45%) of a solid, which was combined with 1.3 g of an additional sample. A 2.0 g sample was dissolved in absolute ethanol (50 ml) and fumaric acid (0.54 g) was added. The solution was warmed on a steam bath for 10 minutes and stirred at ambient temperature for 1 hour. The resultant solid was collected and dried to afford 1.9 g (34%) of product. A recrystallization from absolute ethanol and anhydrous ether provided 1.4 g (25%) of 3-{4-[4,4-bis(4-fluorophenyl)butyl]-1-piperazinyl}-5-methoxy-2H-indazole fumarate, mp 193°–195° C.

ANALYSIS:

| | | | |
|---|---|---|---|
| Calculated for $C_{28}H_{30}F_2N_4O\cdot C_4H_4O_4$: | 64.85% C | 5.78% H | 9.45% N |
| Found: | 64.38% C | 5.64% H | 9.32% N |

EXAMPLE 43

6-Fluoro-3-{4-(6-fluoro-1,2-benzisoxazol-3-yl)propyl]-1-piperazinyl)-1H-indazole A mixture of 6-fluoro-3-(1-piperazinyl)-1(4.8 g, 0.0218 mol), 3-(3-chloropropyl)-6-fluoro-1,2-benzisoxazole (5.1 g, 0.0240 mol), potassium carbonate (3.6 g, 0.0262 mol) and DMF (100 ml) was stirred at 75° under $N_2$ for 4 hours. The reactin stood at room temperature for 68 hours and was then poured into $H_2O$. The aqueous mixture was extracted with ethyl acetate and the organic extract was washed with $H_2O$, dried with $MgSO_4$ and concentrated to yield 9.8 g of a wet solid. The sample was purified by Preparative HPLC (Water's Associates Prep. LC/System 500A, utilizing 2 silica gel columns and 6% methanol-$CH_2Cl$ as eluent) to provide 2.1 g (24%) of 6-fluoro-3-{4-(6-fluoro-1,2-benzisoxazol-3-yl)propyl]-1-piperazinyl)-1H-indazole, mp 170°–172° C.

ANALYSIS:

| | | | |
|---|---|---|---|
| Calculated for $C_{21}H_{21}F_2N_5O$: | 63.47% C | 5.33% H | 17.62% N |
| Found: | 63.04% C | 5.34% H | 17.47% N |

EXAMPLE 44

1-Benzoyl-3-{4-[4,4-bis(4-fluorophenyl)butyl]-1-piperazinyl}-6-fluoro-1H-indazole hydrochloride A mixture of 3-{4[4,4-bis(4-fluorophenyl)butyl]-1-piperazinyl}-6-fluoro-1H-indazole (3.7 g, 0.008 mol) of Example 36 and benzoyl chloride (18.2 g, 0.129 mol) was warmed on a steam bath under $N_2$ for 2 hours. The reaction was cooled to room temperature and the only residue was diluted with ether. The product was isolated by vacuum filtration and the filter cake was washed well with ether affording 4.2 g of a solid. The product was recrystallized twice from ethanol to provide 2.7 g (50%) of 1-benzoyl-3-{4-[4,4-bis(4-fluorophenyl)butyl]-1-piperazinyl-6-fluoro-1H-indazole hydrochloride, mp 236°–238° C.

ANALYSIS:

| | | | |
|---|---|---|---|
| Calculated for $C_{34}H_{31}F_3N_4\cdot HCl$: | 67.49% C | 5.33% H | 9.26% N |
| Found: | 67.24% C | 5.08% H | 9.15% N |

EXAMPLE 45

1-Benzoyl-3-{4-[4,4-bis(4-fluorophenyl)butyl]-1-piperazinyl}-1H-indazole hydrochloride A mixture of 3-{4-[4,4-bis(4-fluorophenyl)butyl]-1-piperazinyl}-1H-indazole of Example 31 (4.0 g, 0.0090 mol) and benzoyl chloride (24.2 g, 0.1723 mol) was warmed on a steam bath for 2 hours, under $N_2$. The oily residue was triturated with anhydrous ether and filtered. The product was dried to give 5.2 g of a solid. Two consecutive recrystallizations from absolute ethanol provided 4.0 g (75%) of 1-benzoyl-3-{4-[4,4-bis(4-fluorophenyl)butyl]-1-piperazinyl}-1H-indazole hydrochloride, mp 229°–231° C.

ANALYSIS:

| | | | |
|---|---|---|---|
| Calculated for $C_{34}H_{32}F_2N_4O\cdot HCl$: | 69.54% C | 5.68% H | 9.54% N |
| Found: | 69.61% C | 5.63% H | 9.52% N |

EXAMPLE 46

5-Bromo-3-(4-methyl-1-piperazinyl)-1H-indazole hydrochloride

A mixture of 3-(4-methyl-1-piperazinyl)-5-bromo-1-phenylsulfonyl)-1H-indazole (8.0 g, 0.0184 mol) of Example 4c, milled KOH (1.6 g, 0.0294 mol) and tetrahydrofuran (THF) [150 ml] was stirred at reflux for 6 hours. The cooled reaction was filtered and the filter cake was washed well with fresh THF. The filtrate was concentrated to afford an oily residue which was diluted with $H_2O$ (100 ml). The aqueous mixture was extracted with ethyl acetate and the organic extract was washed with $H_2O$, dried with $MgSO_4$ and concentrated to yield 4.4 g of a solid. The solid was taken up in anhydrous ether and a minimal amount of methanol. After filtering away some particulate matter, the solution was stirred vigorously while ethanol HCl was added. When the mixture became acidic a solid formed and was collected by filtration. The product was dried in a vacuum oven overnight to give 4.8 g of solid. The product was recrystallized from ethanol-ether to yield 3.5 g. Subsequent recrystallization from ethanol provided 2.0 g (33%) of 5-bromo-3-(4-methyl-1-piperazinyl)-1H-indazole hydrochloride, mp 271°–273° C.

ANALYSIS:

| | | | |
|---|---|---|---|
| Calculated for $C_{12}H_5BrN_4\cdot HCl$: | 43.46% C | 4.86% H | 16.89% N |
| Found: | 43.65% C | 4.83% H | 16.85% N |

We claim:

1. A compound of the formula

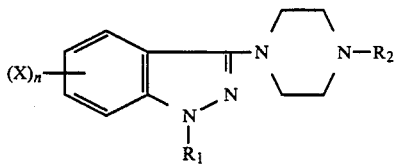

wherein R₁ is hydrogen, lower alkyl, arylloweralkyl, acyl, cycloalkylloweralkylene, and phenylsulfonyl; wherein the term "aryl" signifies a phenyl group optionally substituted by one or more hydrogen or halogen atoms or loweralkyl, loweralkoxy, trifluoromethyl, nitro or amino groups; the term "cycloalkyl" refers to a saturated hydrocarbon possessing at least one carbocyclic ring of three to seven carbon atoms; and the term "acyl" refers to a substituent having the formula loweralkyl

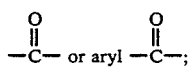

and R₂ is hydrogen, lower alkyl, hydroxyloweralkyl of the formula

‑(loweralkylene)‑OH, arylloweralkyl, acyl, cycloalkylloweralkylene, ‑(loweralkylene)‑N 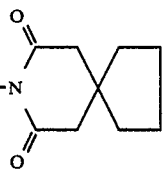

‑(loweralkylene)‑CH 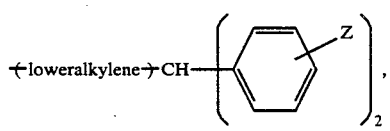

where Z is selected from hydrogen, halogen, loweralkoxy, CF₃, NO₂ and NH₂;

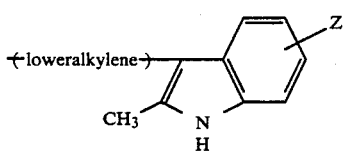

where Z is as defined above,

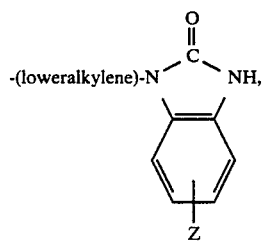

where Z is as defined above;

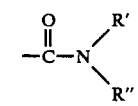

where R₃ and R₄ are each independently hydrogen and loweralkyl;

where Z is as defined above;

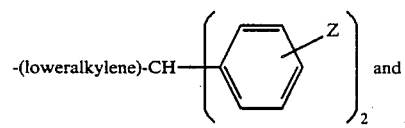

where R' and R'' are each independently hydrogen and loweralkyl; X is hydrogen, loweralkyl, hydroxyl, halogen, loweralkoxy, CF₃, NO₂; n is an integer of 1 to 4, with the proviso that if X is a chlorine atom attached at the 5 or 6 position of the benzene ring, R₂ cannot be hydrogen or loweralkyl and R₁ cannot be hydrogen or $$\text{loweralkyl-}\overset{O}{\underset{\|}{C}}\text{—},$$

the pharmaceutically acceptable acid addition salts thereof; and where applicable the geometric and optical isomers thereof and the racemic mixtures thereof.

2. The compound as defined in claim 1 wherein R₁ is selected from hydrogen, lower alkyl and benzoyl and R₂ is selected from loweralkyl.

3. The compound as defined in claim 1 wherein R₁ is selected from hydrogen and loweralkyl and R₂ is selected from arylloweralkyl and

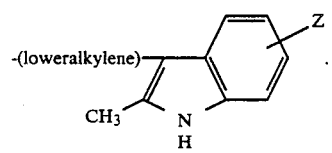 and

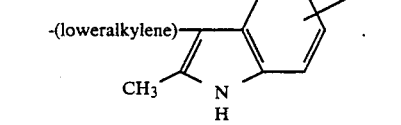

4. The compound as defined in claim 1 which is 1-methyl-3-(1-piperazinyl)-1H-indazole or the pharmaceutically acceptable acid addition salts thereof.

5. The compound as defined in claim 1 which is 8-[4-[1-(1-methyl-1H-indazol-3-yl)-4-piperazinyl]butyl-8-azaspiro[4.5]decane-7,9-dione or the pharmaceutically acceptable acid addition salts thereof.

6. The compound as defined in claim 5 wherein said salt is the fumarate.

7. The compound as defined in claim 1 which is 8-[4-[1-(1-H-indazol-3-yl)-4-piperazinyl]butyl-8-azaspiro[4.5]decane-7,9-dione or the pharmaceutically acceptable acid addition salts thereof.

8. The compound as defined in claim 7 wherein said salt is the hemifumarate.

9. The compound as defined in claim 1 which is 1-acetyl-5-methoxy-3-(4-methyl-1-piperazinyl)-1H-indazole or the pharmaceutically acceptable acid addition salts thereof.

10. The compound as defined in claim 9 wherein said salt is the hydrochloride.

11. The compound as defined in claim 1 which is 5-methoxy-3-(4-methyl-1-piperazinyl)-1H-indazole or the pharmaceutically acceptable acid addition salts thereof.

12. The compound as defined in claim 1 which is 1-benzoyl-5-methoxy-3-(4-methyl-1-piperazinyl)-1H-indazole.

13. The compound as defined in claim 12 wherein said salt is the hydrochloride.

14. The compound as defined in claim 1 which is 5-methoxy-3-{4-[3-(2-methylindol-3-yl)propyl]-1-piperazinyl}-1H-indazole or the pharmaceutically acceptable acid addition salts thereof.

15. The compound as defined in claim 14 wherein said salt is the hemifumarate.

16. The compound as defined in claim 1 which is 5-methoxy-3-{4-[3-(1,3-dihydro-2-oxo-2H-benzimidazol-1-yl)propyl]-1-piperazinyl}-1H-indazole or the pharmaceutically acceptable acid addition salts thereof.

17. The compound as defined in claim 16 wherein said salt is the hemifumarate.

18. The compound as defined in claim 1 which is 3-(4-methyl-1-piperazinyl)-1H-indazole or the pharmaceutically acceptable acid addition salts thereof.

19. The compound as defined in claim 1 which is 1-acetyl-3-(4-methyl-1-piperazinyl)-1H-indazole or the pharmaceutically acceptable acid addition salts thereof.

20. The compound as defined in claim 1 which is 1-benzoyl-3-(4-methyl-1-piperazinyl)-1H-indazole or the pharmaceutically acceptable acid addition salts thereof.

21. The compound as defined in claim 1 which is 1-ethyl-3-(4-methyl-1-piperazinyl)-1H-indazole or the pharmaceutically acceptable acid addition salts thereof.

22. The compound as defined in claim 21 wherein said salt is the hydrochloride.

23. The compound as defined in claim 1 which is 1-methyl-3-(4-methyl-1-piperazinyl)-1H-indazole or the pharmaceutically acceptable acid addition salts thereof.

24. The compound as defined in claim 23 wherein said salt is the hydrochloride.

25. The compound as defined in claim 1 which is 1-cyclopropylmethyl-3-(4-methyl-1-piperazinyl)-1H-indazole.

26. The compound as defined in claim 1 which is 1-benzoyl-5-chloro-3-(4-methyl-1-piperazinyl)-1H-indazole or the pharmaceutically acceptable acid addition salts thereof.

27. The compound as defined in claim 1 which is 3-(1-piperazinyl)-1H-indazole or the pharmaceutically acceptable acid addition salts thereof.

28. The compound as defined in claim 1 which is 3-{4-[3-(1,3-dihydro-2-oxo-2H-benzimidazol-1-yl)propyl]-1-piperazinyl}-1H-indazole or the pharmaceutically acceptable acid addition salts thereof.

29. The compound as defined in claim 1 which is 4-(1H-indazol-3-yl)-1-piperazinecarboxamide.

30. The compound as defined in claim 1 which is 3-[4-(2-hydroxyethyl)-1-piperazinyl]-1H-indazole or the pharmaceutically acceptable acid addition salts thereof.

31. The compound as defined in claim 30 wherein said salt is the dihydrochloride.

32. The compound as defined in claim 1 which is 3-[4-(dimethylphosphinylmethyl)-1-piperazinyl]-1H-indazole or the pharmaceutically acceptable acid addition salts thereof.

33. The compound as defined in claim 1 which is 3-{4-[3-(2-methylindol-3-yl)propyl]-1-piperazinyl}-1H-indazole or the pharmaceutically acceptable acid addition salts thereof.

34. The compound as defined in claim 33 wherein said salt is the hemifumarate.

35. The compound as defined in claim 1 which is 3-(4-ethyl-1-piperazinyl)-1H-indazole or the pharmaceutically acceptable acid addition salts thereof.

36. The compound as defined in claim 1 which is 3-[4-(2-phenylethyl)-1-piperazinyl]-1H-indazole or the pharmaceutically acceptable acid addition salts thereof.

37. The compound as defined in claim 1 which is 3-{4-[3-(6-fluoro-1,2-benzisoxazol-3-yl)propyl]-1-piperazinyl}-1H-indazole or the pharmaceutically acceptable acid addition salts thereof.

38. The compound as defined in claim 1 which is 3-[4-[4,4-bis(4-fluorophenyl)butyl]-1-piperazinyl]-1H-indazole or the pharmaceutically acceptable acid addition salts thereof.

39. The compound as defined in claim 38 wherein said salt is the hydrochloride.

40. The compound as defined in claim 1 which is 6-fluoro-3-(4-methyl-1-piperazinyl)-1H-indazole or the pharmaceutically acceptable acid addition salts thereof.

41. The compound as defined in claim 1 which is 1-benzoyl-6-fluoro-3-(4-methyl-1-piperazinyl)-1H-indazole or the pharmaceutically acceptable acid addition salts thereof.

42. The compound as defined in claim 1 which is 6-fluoro-3-(1-piperazinyl)-1H-indazole or the pharmaceutically acceptable acid addition salts thereof.

43. The compound as defined in claim 42 wherein said salt is the hydrochloride.

44. The compound as defined in claim 1 which is 6-fluoro-3-{4-[3-(1,3-dihydro-2-oxo-2H-benzimidazol-1-yl)propyl]-1-piperazinyl-1-H-indazole or the pharmaceutically acceptable acid addition salts thereof.

45. The compound as defined in claim 44 wherein said salt is the hemifumarate.

46. The compound as defined in claim 1 which is 3-[4-[4,4-bis(4-fluorophenylbutyl]-1-piperazinyl]-6-fluoro-1H-indazole or the pharmaceutically acceptable acid addition salts thereof.

47. The compound as defined in claim 46 wherein said salt is the hydrochloride.

48. The compound as defined in claim 1 which is 3-{4-[4,4-bis(4-fluorophenyl)butyl]-1-piperazinyl}-5-chloro-1H-indazole or the pharmaceutically acceptable acid addition salts thereof.

49. The compound as defined in claim 48 wherein said salt is the hydrochloride.

50. The compound as defined in claim 1 which is 6-chloro-3-(4-methyl-1-piperazinyl)-1-phenylsulfonyl-1H-indazole or the pharmaceutically acceptable acid addition salts thereof.

51. The compound as defined in claim 1 which is 3-{4-[4,4-bis(4-fluorophenyl)butyl]-1-piperazinyl}-6- chloro-1H-indazole or the pharmaceutically acceptable acid addition salts thereof.

52. The compound as defined in claim 1 wherein said salt is the hemifumarate.

53. The compound as defined in claim 1 which is 1-benzoyl-3-{4-[4,4-bis(4-fluorophenyl)butyl]-1-piperazinyl}-6-chloro-1H-indazole or the pharmaceutically acceptable acid addition salts thereof.

54. The compound as defined in claim 53 wherein said salt is the hydrochloride.

55. The compound as defined in claim 1 which is 3-{4-[4,4-bis(4-fluorophenyl)butyl]-1-piperazinyl}-5-methoxy-1H-indazole or the pharmaceutically acceptable acid addition salts thereof.

56. The compound as defined in claim 55 wherein said salt is the fumarate.

57. The compound as defined in claim 1 which is 6-fluoro-3-{4-(6-fluoro-1,2-benzisoxazol-3-yl)propyl]-piperazinyl}-1H-indazole or the pharmaceutically acceptable acid addition salts thereof.

58. The compound as defined in claim 1 which is 1-benzoyl-3-{4-[4,4-bis(4-fluorophenyl)butyl]-1-piperazinyl}-6-fluoro-1H-indazole or the pharmaceutically acceptable acid addition salts thereof.

59. The compound as defined in claim 58 wherein said salt is the hydrochloride.

60. The compound as defined in claim 1 which is 1-benzoyl-3-{4-[4,4-bis(4-fluorophenyl)butyl]-1-piperazinyl}-1H-indazole or the pharmaceutically acceptable acid addition salts thereof.

61. The compound as defined in claim 60 wherein said salt is the hydrochloride.

62. The compound as defined in claim 1 which is 5-bromo-3-(4-methyl-1-piperazinyl)-1H-indazole or the pharmaceutically acceptable acid addition salts thereof.

63. The compound as defined in claim 62 wherein said salt is the hydrochloride.

64. An analgesic composition which comprises an effective pain alleviating amount of a compound as defined in claim 1 and a suitable carrier therefor.

65. The composition defined in claim 64 wherein $R_1$ is selected from hydrogen, loweralkyl and benzoyl and $R_2$ is selected from loweralkyl.

66. The composition as defined in claim 64 wherein $R_1$ is selected from hydrogen and loweralkyl and $R_2$ is selected from aryl loweralkyl and

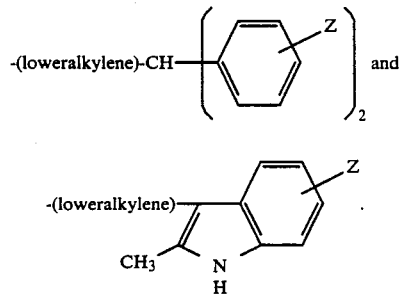

67. The composition as defined in claim 64 wherein said compound is 1-methyl-3-(1-piperazinyl)-1H-indazole or the pharmaceutically acceptable acid addition salts thereof.

68. The composition as defined in claim 64 wherein said compound is 8-[4-[1-(1-methyl-1H-indazol-3-yl)-3-piperazinyl]butyl]-8-azaspiro[4.5]decane-7,9-dione or the pharmaceutically acceptable acid addition salts thereof.

69. The composition as defined in claim 68 wherein said compound is the fumarate.

70. The composition as defined in claim 64 wherein said compound is 8-[4-[1-(1H-indazol-3-yl)-4-piperazinyl]butyl-8-azaspiro[4.5]decane-7,9-dione or the pharmaceutically acceptable acid addition salts thereof.

71. The composition as defined in claim 70 wherein said compound is the hemifumarate.

72. The composition as defined in claim 64 wherein said compound is 1-acetyl-5-methoxy-3-(4-methyl-1-piperazinyl)-1H-indazole or the pharmaceutically acceptable acid addition salts thereof.

73. The composition as defined in claim 72 wherein said compound is the hydrochloride.

74. The composition as defined in claim 64 wherein said compound is 5-methoxy-3-(4-methyl-1-piperazinyl)-1H-indazole or the pharmaceutically acceptable acid addition salts thereof.

75. The composition as defined in claim 64 wherein said compound is 1-benzoyl-5-methoxy-3-(4-methyl-1-piperaziny)-1H-indazole.

76. The composition as defined in claim 75 wherein said compound is the hydrochloride.

77. The composition as defined in claim 64 wherein said compound is 5-methoxy-3-{4-[3-(2-methylindol-3-yl)propyl]-1-piperazinyl}-1H-indazole or the pharmaceutically acceptable acid addition salts thereof.

78. The composition as defined in claim 77 wherein said compound is the hemifumarate.

79. The composition as defined in claim 64 wherein said compound is 5-methoxy-3-{4-[3-(1,3-dihydro-2-oxo-2H-benzimidazol-1-yl)propyl]-1-piperazinyl}-1H-indazole or the pharmaceutically acceptable acid addition salts thereof.

80. The composition as defined in claim 79 wherein said compound is the hemifumarate.

81. The composition as defined in claim 64 wherein said compound is 3-(4-methyl-1-piperazinyl)-1H-indazole or the pharmaceutically acceptable acid addition salts thereof.

82. The composition as defined in claim 64 wherein said compound is 1-acetyl-3-(4-methyl-1-piperazinyl)-1H-indazole or the pharmaceutically acceptable acid addition salts thereof.

83. The composition as defined in claim 64 wherein said compound is 1-benzoyl-3-(4-methyl-1-piperazinyl)-1H-indazole or the pharmaceutically acceptable acid addition salts thereof.

84. The composition as defined in claim 64 wherein said compound is 1-ethyl-3-(4-methyl-1-piperazinyl)-1H-indazole or the pharmaceutically acceptable acid addition salts thereof.

85. The composition as defined in claim 84 wherein said compound is the hydrochloride.

86. The composition as defined in claim 64 wherein said compound is 1-methyl-3-(4-methyl-1-piperazinyl)-1H-indazole or the pharmaceutically acceptable acid addition salts thereof.

87. The composition as defined in claim 86 wherein said compound is the hydrochloride.

88. The composition as defined in claim 64 wherein said compound is 1-cyclopropylmethyl-3-(4-methyl-1-piperazinyl)-1H-indazole.

89. The composition as defined in claim 64 wherein said compound is 1-benzoyl-5-chloro-3-(4-methyl-1-piperazinyl)-1H-indazole or the pharmaceutically acceptable acid addition salts thereof.

90. The composition as defined in claim 64 wherein said compound is 3-(1-piperazinyl)-1H-indazole or the pharmaceutically acceptable acid addition salts thereof.

91. The composition as defined in claim 64 wherein said compound is 3-{4-[3-(1,3-dihydro-2-oxo-2H-benzimidazol-1-yl)propyl]-1-piperazinyl}-1H-indazole or the pharmaceutically acceptable acid addition salts thereof.

92. The composition as defined in claim 64 wherein said compound is 4-(1H-indazol-3-yl)-1-piperazinecarboxamide.

93. The composition as defined in claim 64 wherein said compound is 3-[4-(2-hydroxyethyl)-1-piperazinyl]-1H-indazole or the pharmaceutically acceptable acid addition salts thereof.

94. The composition as defined in claim 93 wherein said compound is the dihydrochloride.

95. The composition as defined in claim 64 wherein said compound is 3-[4-(dimethyl phosphinylmethyl)-1-piperazinyl]-1H-indazole or the pharmaceutically acceptable acid addition salts thereof.

96. The composition as defined in claim 95 wherein said compound is the hemifumarate.

97. The composition as defined in claim 64 wherein said compound is 3-(4-ethyl-1-piperazinyl)-1H-indazole or the pharmaceutically acceptable acid addition salts thereof.

98. The composition as defined in claim 64 wherein said compound is 3-[4-(2-phenylethyl)-1-piperazinyl]-1H-indazole or the pharmaceutically acceptable acid addition salts thereof.

99. The composition as defined in claim 64 wherein said compound is 3-{4-[3-(6-fluoro-1,2-benzisoxazol-3-yl)propyl]-1-piperazinyl}-1H-indazole or the pharmaceutically acceptable acid addition salts thereof.

100. The composition as defined in claim 64 wherein said compound is 3-[4-[4,4-bis(4-fluorophenyl)butyl]-1-piperazinyl]-1H-indazole or the pharmaceutically acceptable acid addition salts thereof.

101. The composition as defined in claim 100 wherein said compound is the hydrochloride.

102. The composition as defined in claim 64 wherein said compound is 6-fluoro-3-(4-methyl-1-piperazinyl)-1H-indazole or the pharmaceutically acceptable acid addition salts thereof.

103. The composition as defined in claim 64 wherein said compound is 1-benzoyl-6-fluoro-3-(4-methyl-1-piperazinyl)-1H-indazole or the pharmaceutically acceptable acid addition salts thereof.

104. The composition as defined in claim 64 wherein said compound is 6-fluoro-3-(1-piperazinyl)-1H-indazole or the pharmaceutically acceptable acid addition salts thereof.

105. The composition as defined in claim 104 wherein said compound is the hydrochloride.

106. The composition as defined in claim 64 wherein said compound is 6-fluoro-3-{4-[3-(1,3-dihydro-2-oxo-2H-benzimidazol-1-yl)propyl]-1-piperazinyl}-1H-indazole or the pharmaceutically acceptable acid addition salts thereof.

107. The composition as defined in claim 106 wherein said compound is the hemifumarate.

108. The composition as defined in claim 64 wherein said compound is 3-[4-[4,4-bis(4-fluorophenyl)butyl]-1-piperazinyl]-6-fluoro-1H-indazole or the pharmaceutically acceptable acid addition salts thereof.

109. The composition as defined in claim 108 wherein said compound is the hydrochloride.

110. The composition as defined in claim 64 wherein said compound is 3-{4-[4,4-bis(4-fluorophenyl)butyl]-1-piperazinyl}-5-chloro-1H-indazole or the pharmaceutically acceptable acid addition salts thereof.

111. The composition as defined in claim 64 wherein said compound is 6-chloro-3-(4-methyl-1-piperazinyl)-6-chloro-1-phenylsulfonyl-1H-indazole or the pharmaceutically acceptable acid addition salts thereof.

112. The composition as defined in claim 64 wherein said compound is 1-benzoyl-3-{4-[4,4-bis(4-fluorophenyl)butyl]-1-piperazinyl}-6-chloro-1H-indazole or the pharmaceutically acceptable acid addition salts thereof.

113. The composition as defined in claim 112 wherein said salt is the hydrochloride.

114. The composition as defined in claim 64 wherein said compound is 3-{4-[4,4-bis(4-fluorophenyl)butyl]-1-piperazinyl}-5-methoxy-1H-indazole or the pharmaceutically acceptable acid addition salts thereof.

115. The composition as defined in claim 114 wherein said compound is the fumarate.

116. The composition as defined in claim 64 wherein said compound is 6-fluoro-3-{4-(6-fluoro-1,2-benzisoxazol-3-yl)-propyl]piperazinyl}-1H-indazole or the pharmaceutically acceptable acid addition salts thereof.

117. The composition as defined in claim 64 wherein said compound is 1-benzoyl-3-{4-[4,4-bis(4-fluorophenyl)butyl]-1-piperazinyl}-6-fluoro-1H-indazole or the pharmaceutically acceptable acid addition salts thereof.

118. The composition as defined in claim 117 wherein said salt is the hydrochloride.

119. The composition as defined in claim 64 wherein said compound is 1-benzoyl-3-{4-[4,4-bis(4-fluorophenyl)butyl]-1-piperazinyl}-1H-indazole or the pharmaceutically acceptable acid addition salts thereof.

120. The composition as defined in claim 119 wherein said salt is the hydrochloride.

121. The composition as defined in claim 64 wherein said compound is 5-bromo-3-(4-methyl-1-piperazinyl)-1H-indazole or the pharmaceutically acceptable acid addition salts thereof.

122. The composition as defined in claim 121 wherein said salt is the hydrochloride.

123. An antipsychotic composition which comprises an effective psychoses alleviating amount of a compound as defined in claim 1 and a suitable carrier therefore.

124. The composition as defined in claim 123 wherein $R_1$ is selected from hydrogen, loweralkyl and benzoyl and $R_2$ is selected from loweralkyl.

125. The composition as defined in claim 123 wherein $R_1$ is selected from hydrogen and loweralkyl and $R_2$ is selected from $$\text{-(loweralkylene)-CH} \underset{2}{\overbrace{\left( \underset{}{\underset{}{\bigcirc}} Z \right)}} \text{ and}$$

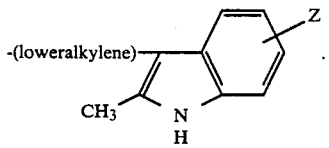

126. The composition as defined in claim 123 wherein said compound is 1-methyl-3-(1-piperazinyl)-1H-indazole or the pharmaceutically acceptable acid addition salts thereof.

127. The composition as defined in claim 123 wherein said compound is 8-[4-[1-(1-methyl-1H-indazol-3-yl)-4-piperazinyl]butyl-8-azaspiro[4:5]decane-7,9-dione or the pharmaceutically acceptable acid addition salts thereof.

128. The composition as defined in claim 127 wherein said compound is the fumarate.

129. The composition as defined in claim 123 wherein said compound is 8-[4-[1-(1H-indazol-3-yl)-4-piperazinyl]butyl-8-azaspiro[4.5]decane-7,9-dione or the pharmaceutically acceptable acid addition salts thereof.

130. The composition as defined in claim 129 wherein said salt is the hemifumarate.

131. The composition as defined in claim 123 wherein said compound is 1-acetyl-5-methoxy-3-(4-methyl-1-piperazinyl)-1H-indazole or the pharmaceutically acceptable acid addition salts thereof.

132. The composition as defined in claim 131 wherein said compound is hydrochloride.

133. The composition as defined in claim 123 wherein said compound is 5-methoxy-3-(4-methyl-1-piperazinyl)-1H-indazole or the pharmaceutically acceptable acid addition salts thereof.

134. The composition as defined in claim 123 wherein said compound is 5-methoxy-3-{4-[3-(2-methylindol-3-yl)propyl]-1-piperazinyl}-1H-indazole or the pharmaceutically acceptable acid addition salts thereof.

135. The composition as defined in claim 135 wherein said compound is the hemifumarate.

136. The composition as defined in claim 123 wherein said compound is 3-{4-[3-(2-methylindol-3yl)propyl]-1-piperazinyl}-1H-indazole or the pharmaceutically acceptable acid addition salts thereof.

137. The composition as defined in claim 136 wherein said compound is the hemifumarate.

138. The composition as defined in claim 123 wherein said compound is 5-methoxy-3-{4-[3-(1,3-dihydro-2-oxo-2H-benzimidazol-1-yl)propyl]-1-piperazinyl}-1H-indazole or the pharmaceutically acceptable acid addition salts thereof.

139. The composition as defined in claim 138 wherein said compound is the hemifumarate.

140. The composition as defined in claim 123 wherein said compound is 3-(4-methyl-1-piperazinyl)-1H-indazole or the pharmaceutically acceptable acid addition salts thereof.

141. The composition as defined in claim 123 wherein said compound is 1-acetyl-3-(4-methyl-1-piperazinyl)-1H-indazole or the pharmaceutically acceptable acid addition salts thereof.

142. The composition as defined in claim 123 wherein said compound is 1-benzoyl-3-(4-methyl-1-piperazinyl)-1H-indazole or the pharmaceutically acceptable acid addition salts thereof.

143. The composition as defined in claim 123 wherein said compound is 1-ethyl-3-(4-methyl-1-piperazinyl)-1H-indazole or the pharmaceutically acceptable acid addition salts thereof.

144. The composition as defined in claim 143 wherein said compound is the hemifumarate.

145. The composition as defined in claim 123 wherein said compound is 1-methyl-3-(4-methyl-1-piperazinyl)-1H-indazole or the pharmaceutically acceptable acid addition salts thereof.

146. The composition as defined in claim 145 wherein said compound is the hydrochloride.

147. The composition as defined in claim 123 wherein said compound is 1-cyclopropylmethyl-3-(4-methyl-1-piperazinyl)-1H-indazole.

148. The composition as defined in claim 123 wherein said compound is 1-benzoyl-5-chloro-3-(4-methyl-1-piperazinyl)-1H-indazole or the pharmaceutically acceptable acid addition salts thereof.

149. The composition as defined in claim 123 wherein said compound is 3-(1-piperazinyl)-1H-indazole or the pharmaceutically acceptable acid addition salts thereof.

150. The composition as defined in claim 123 wherein said compound is 3-{4-[3-(1,3-dihydro-2-oxo-2H-benzimidazol-1-yl)propyl]-1-piperazinyl}-1H-indazole or the pharmaceutically acceptable acid addition salts thereof.

151. The composition as defined in claim 123 wherein said compound is 4-(1H-indazol-3-yl)-1-piperazinecarboxamide.

152. The composition as defined in claim 123 wherein said compound is 3-[4-(2-hydroxyethyl)-1-piperazinyl]-1H-indazole or the pharmaceutically acceptable acid addition salts thereof.

153. The composition as defined in claim 152 wherein said compound is the dihydrochloride.

154. The composition as defined in claim 123 wherein said compound is 3-[4-(dimethylphosphinylmethyl)-1-piperazinyl]-1H-indazole or the pharmaceutically acceptable acid addition salts thereof.

155. The composition as defined in claim 123 wherein said compound is 3-{4-[3-(2-methylindol-3-yl)propyl]-1-piperazinyl}-1H-indazole or the pharmaceutically acceptable acid addition salts thereof.

156. The composition as defined in claim 155 wherein said compound is the hemifumarate.

157. The composition as defined in claim 123 wherein said compound 3-(4-ethyl-1-piperazinyl)-1H-indazole or the pharmaceutically acceptable acid addition salts thereof.

158. The composition as defined in claim 123 wherein said compound is 3-[4-(2-phenylethyl)-1-piperazinyl]-1H-indazole or the pharmaceutically acceptable acid addition salts thereof.

159. The composition as defined in claim 123 wherein said compound is 3-{4-[3-(6-fluoro-1,2-benzisoxazol-3-yl)propyl]-1-piperazinyl}-1H-indazole or the pharmaceutically acceptable acid addition salts thereof.

160. The composition ad defined in claim 123 wherein said compound is 3-[4-[4,4-bis(4-fluorophenyl)butyl]-1-piperazinyl]-1H-indazole or the pharmaceutically acceptable acid addition salts thereof.

161. The composition as defined in claim 160 wherein said compound is the hydrochloride.

162. The composition as defined in claim 123 wherein said compound is 6-fluoro-3-(4-methyl-1-piperazinyl)-1H-indazole or the pharmaceutically acceptable acid addition salts thereof.

163. The composition as defined in claim 123 wherein said compound is 1-benzoyl-6-fluoro-3-(4-methyl-1-piperazinyl)-1H-indazole or the pharmaceutically acceptable acid addition salts thereof.

164. The composition as defined in claim 123 wherein said compound is 6-fluoro-3-(1-piperazinyl)-1H-indazole or the pharmaceutically acceptable acid addition salts thereof.

165. The composition as defined in claim 164 wherein said compound is the hydrochloride.

166. The composition as defined in claim 123 wherein said compound is 6-fluoro-3-{4-[3-(1,3-dihydro-2-oxo-2H-benzimidazol-1-yl)propyl]-1-piperazinyl}-1H-indazole or the pharmaceutically acceptable acid addition salts thereof.

167. The composition as defined in claim 166 wherein said compound is the hemifumarate.

168. The composition as defined in claim 123 wherein said compound is 3-[4-[4,4-bis(4-fluorophenyl)butyl]-1-piperazinyl]-6-fluoro-1H-indazole or the pharmaceutically acceptable acid addition salts thereof.

169. The composition as defined in claim 168 wherein said compound is the hydrochloride.

170. The composition as defined in claim 123 wherein said compound is 5-chloro-3-{4-[4,4-bis(4-fluorophenyl)butyl]-1-piperazinyl}-1H-indazole or the pharmaceutically acceptable acid addition salts thereof.

171. The composition as defined in claim 123 wherein said compound is 6-chloro-3-(4-methyl-1-piperazinyl)-1-phenylsulfonyl-1H-indazole or the pharmaceutically acceptable acid addition salts thereof.

172. The composition as defined in claim 123 wherein said compound is 3-{4-[4,4-bis(4-fluorophenyl)butyl]-1-piperazinyl}-6-chloro-1H-indazole or the pharmaceutically acceptable acid addition salts thereof.

173. The composition of claim 172 wherein said salt is the hemifumarate.

174. The composition as defined in claim 123 wherein said compound is 1-benzoyl-3-{4-[4,4-bis(4-fluorophenyl)butyl]-1-piperazinyl}-6-chloro-1H-indazole or the pharmaceutically acceptable acid addition salts thereof.

175. The composition as defined in claim 174 wherein said salt is the hydrochloride.

176. The composition as defined in claim 123 wherein said compound is 3-{4-[4,4-bis(4-fluorophenyl)butyl]-1-piperazinyl}-5-methoxy-1H-indazole or the pharmaceutically acceptable acid addition salts thereof.

177. The composition as defined in claim 176 wherein said salt is the fumarate.

178. The composition as defined in claim 123 wherein said compound is 6-fluoro-3-{4-(6-fluoro-1,2-benzisoxazol-3-yl)propyl]-piperazinyl}-1H-indazole or the pharmaceutically acceptable acid addition salts thereof.

179. The composition as defined in claim 123 wherein said compound is 1-benzoyl-3-{4-[4,4bis(4-fluorophenyl)butyl]-1-piperazinyl}-6-fluoro-1H-indazole or the pharmaceutically acceptable acid addition salts thereof.

180. The composition as defined in claim 179 wherein said salt is the hydrochloride.

181. The composition as defined in claim 123 wherein said compound is 1-benzoyl-3-{4-[4,4-bis(4-fluorophenyl)butyl]-1-piperazinyl}-1H-indazole or the pharmaceutically acceptable acid addition salts thereof.

182. The composition as defined in claim 181 wherein said salt is the hydrochloride.

183. The composition as defined in claim 123 wherein said compound is 5-bromo-3-(4-methyl-1-piperazinyl)-1H-indazole or the pharmaceutically acceptable acid addition salts thereof.

184. The composition as defined in claim 183 wherein said salt is the hydrochloride.

185. A method of alleviating pain in a mammal which comprises administering a pain alleviating amount of a compound as defined in claim 1.

186. A method of alleviating psychoses in a mammal in need thereof which comprises administering to the mammal a psychoses alleviating amount of a compound as defined in claim 1.

187. A compound of the formula

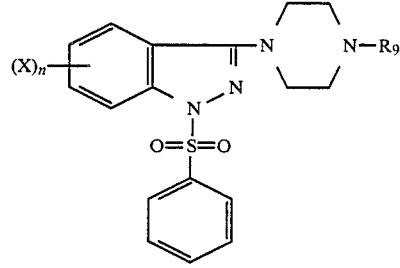

wherein $R_9$ is loweralkyl, CN and n is an integer of 1 to 4; and X is hydrogen, loweralkyl, hydroxy, halogen, loweralkoxy, $CF_3$, $NO_2$, $NH_2$.

* * * * *